(12) United States Patent
Martynus et al.

(10) Patent No.: US 11,452,643 B2
(45) Date of Patent: Sep. 27, 2022

(54) ABSORBENT ARTICLES WITH IMPROVED LOW VISCOSITY WASTE ACQUISITION

(71) Applicant: The Procter & Gamble Company, Cincinnati, OH (US)

(72) Inventors: Cornelia B. Martynus, Nidderau-Osteheim (DE); Donald C. Roe, West Chester, OH (US); Nathan R. Whitely, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 756 days.

(21) Appl. No.: 16/459,993

(22) Filed: Jul. 2, 2019

(65) Prior Publication Data

US 2021/0000655 A1  Jan. 7, 2021

(51) Int. Cl.
*A61F 13/537* (2006.01)
*A61F 13/15* (2006.01)
(Continued)

(52) U.S. Cl.
CPC ........ *A61F 13/15203* (2013.01); *A61F 13/42* (2013.01); *A61F 13/495* (2013.01);
(Continued)

(58) Field of Classification Search
CPC .......... A61F 13/15203; A61F 13/51104; A61F 13/51108; A61F 13/512; A61F 13/5121; A61F 13/5122; A61F 13/5123; A61F 13/537; A61F 13/53747; A61F 13/5376; A61F 2013/15373; A61F 2013/15552;
(Continued)

(56) References Cited

U.S. PATENT DOCUMENTS

| | | | |
|---|---|---|---|
| 5,342,338 A | 8/1994 | Roe | |
| 5,439,458 A | 8/1995 | Noel et al. | |

(Continued)

FOREIGN PATENT DOCUMENTS

| | | |
|---|---|---|
| CN | 1373650 A | 10/2002 |
| CN | 102361614 A | 2/2012 |

(Continued)

OTHER PUBLICATIONS

International Search Report and Written Opinion; Application Ser. No. PCT/US2020/070139; dated Oct. 1, 2020, 11 pages.

*Primary Examiner* — Catharine L Anderson
*Assistant Examiner* — Lynne Anderson
(74) *Attorney, Agent, or Firm* — Christian M. Best

(57) ABSTRACT

An absorbent article includes a liquid permeable, apertured topsheet, a liquid impermeable backsheet, an absorbent core disposed at least partially intermediate the topsheet and the backsheet, and an acquisition material disposed at least partially intermediate the topsheet and the absorbent core. The acquisition material has a caliper in the range of about 2.5 mm to about 10 mm, according to the Caliper Test, and an Air Permeability in the range of about 5,000 l/m²/s to about 11,000 l/m²/s, according to the Air Permeability Test. The acquisition material has a first surface, a second surface, and a plurality of three-dimensional features extending outwardly from the first surface or the second surface.

16 Claims, 24 Drawing Sheets

(51) Int. Cl.
  *A61F 13/42* (2006.01)
  *A61F 13/495* (2006.01)
  *A61F 13/511* (2006.01)
(52) U.S. Cl.
  CPC ...... *A61F 13/511* (2013.01); *A61F 13/53756* (2013.01); *A61F 2013/15373* (2013.01); *A61F 2013/15463* (2013.01); *A61F 2013/15552* (2013.01); *A61F 2013/422* (2013.01); *A61F 2013/53739* (2013.01)
(58) Field of Classification Search
  CPC ...... A61F 2013/5127; A61F 2013/5128; A61F 2013/53721; A61F 2013/53726; A61F 2013/5373; A61F 2013/53739; A61F 2013/53765; A61F 2013/53773; A61F 2013/53778; A61F 2013/53786
  See application file for complete search history.

(56) References Cited

U.S. PATENT DOCUMENTS

| | | |
|---|---|---|
| 5,490,846 A | 2/1996 | Ellis et al. |
| 5,628,097 A | 5/1997 | Benson et al. |
| 5,941,864 A | 8/1999 | Roe |
| 6,010,491 A | 1/2000 | Roe et al. |
| 6,186,992 B1 | 2/2001 | Roe et al. |
| 7,093,072 B2 | 8/2006 | Haskins |
| 7,132,585 B2 * | 11/2006 | Kudo ............... A61F 13/53747 604/380 |
| 8,759,606 B2 | 6/2014 | Bond et al. |
| 2004/0077247 A1 | 4/2004 | Schmidt et al. |
| 2010/0247844 A1 | 9/2010 | Curro |
| 2010/0310810 A1 | 12/2010 | Bond et al. |
| 2010/0310837 A1 | 12/2010 | Bond et al. |
| 2010/0310845 A1 | 12/2010 | Bond et al. |
| 2010/0312208 A1 | 12/2010 | Bond et al. |
| 2010/0312212 A1 | 12/2010 | Bond et al. |
| 2015/0283003 A1* | 10/2015 | Rosati ............... A61F 13/51104 604/385.01 |
| 2017/0281422 A1* | 10/2017 | Herfert ............... B32B 38/0004 |

FOREIGN PATENT DOCUMENTS

| | | |
|---|---|---|
| WO | 9301781 A1 | 2/1993 |
| WO | 0106974 A1 | 2/2001 |
| WO | WO200190465 | 11/2001 |

* cited by examiner

ABSORBENT ARTICLES WITH IMPROVED LOW VISCOSITY WASTE ACQUISITION

FIELD

The present disclosure is generally directed to absorbent articles with improved low viscosity waste acquisition.

BACKGROUND

Disposable absorbent articles are used to receive and contain bodily wastes (e.g., bowel movements, urine, menses). Some example absorbent articles are diapers, pants, adult incontinence products, sanitary napkins, tampons, panty liners, and absorbent pads. These absorbent articles sometimes receive viscous liquid bodily waste, such as low viscosity feces, for example. In some configurations, the absorbent articles may have an apertured topsheet and a porous sublayer disposed under the topsheet. The porous sublayer may be referred to as an acquisition layer or material. Viscous liquid bodily waste deposited on the apertured topsheet may, to some extent, penetrate the topsheet, primarily through the apertures in the topsheet if the apertures are of a sufficient size, and be partially acquired and stored in the porous acquisition material away from the wearer's skin. Current absorbent articles, due to current acquisition materials, however, typically acquire and store much less than the average amount of low viscosity feces or liquid bodily waste deposited in them by infants, babies, children, and/or adult wearers (together "wearer(s)"). This sometimes leads to leakage of the low viscosity feces or waste from the absorbent articles (e.g., up the back or over the cuffs), undesirable amounts of the low viscosity feces or waste left on the wearer's skin, and/or large amounts of low viscosity feces or waste remaining on the topsheet of the absorbent articles. Accordingly, it would be desirable to produce absorbent articles having acquisition materials capable of acquiring and storing most, if not all, of the low viscosity feces or waste deposited in an absorbent article by a wearer.

SUMMARY

The present disclosure provides absorbent articles comprising acquisition materials that are capable of acquiring and storing most, if not all, of the low viscosity feces or waste deposited in an absorbent article by a wearer. It has been found that absorbent articles having improved sublayers or acquisition materials having sufficient caliper and sufficient air permeability absorb substantially more low viscosity feces or waste than current acquisition materials. The acquisition materials of the present disclosure may function even better when combined with an apertured topsheet having apertures large enough for the low viscosity feces or waste to penetrate therethrough. The acquisition materials may be formed of a single layer or more than one layer. If a certain acquisition material comprises more than one layer, each layer may be the same or different in composition, basis weight, fiber type, caliper, dimensions, density, and/or air permeability. If a certain acquisition material has only one layer, the properties of the acquisition material may be homogeneous throughout its thickness or there may be a gradient of density and/or air permeability throughout its thickness. When an acquisition material has a gradient of air permeability and/or density throughout its thickness, the higher air permeability region and/or the lower density region may typically face the wearer. The acquisition materials may comprise three-dimensional features or be "activated" or "mechanically activated". This may lead to more storage space for low viscosity feces or waste and further improve acquisition and storage, thereby further reducing blowouts and waste on skin.

The present disclosure is directed, in part, to an absorbent article comprising a liquid permeable topsheet that may define apertures, a liquid impermeable backsheet, an absorbent core disposed at least partially intermediate the topsheet and the backsheet, and an acquisition material disposed at least partially intermediate the topsheet and the absorbent core. The acquisition material may have a caliper in the range of about 2 mm to about 10 mm, about 2.5 mm to about 10 mm, about 3 mm to about 10 mm, or about 3.5 mm to about 10 mm, according to the Caliper Test herein. The acquisition material may have an Air Permeability in the range of about 5,000 $l/m^2/s$ to about 11,000 $l/m^2/s$, about 6,000 $l/m^2/s$ to about 11,000 $l/m^2/s$, or about 6,100 $l/m^2/s$ to about 11,000 $l/m^2/s$, according to the Air Permeability Test herein. The acquisition material may comprise a first surface, a second surface, and three-dimensional features extending outwardly from the first surface or the second surface. The three-dimensional features may extend toward the absorbent core or may extend toward the topsheet. In some instances, some three-dimensional features may extend toward the topsheet and other three-dimensional features may extend towards the absorbent core. At least some of, a majority of, or all of the three-dimensional features may have an area in the range of about 20 $mm^2$ to about 150 $mm^2$, or about 30 $mm^2$ to about 100 $mm^2$. At least some of, a majority of, or all of the three-dimensional features may have a largest dimension in the range of about 2 mm to about 20 mm, or about 4 mm to about 10 mm.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting forms of the present disclosure will now be described to provide an overall understanding of the principles of the structure, function, manufacture, and use of the Absorbent Articles With Improved Low Viscosity Waste Acquisition disclosed herein. One or more examples of these non-limiting forms are illustrated in the accompanying drawings. Those of ordinary skill in the art will understand that the Absorbent Articles With Improved Low Viscosity Waste Acquisition described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

First, example absorbent articles will be discussed, followed by a discussion of the acquisition materials of the present disclosure.

General Description of an Absorbent Article

Figure 1:
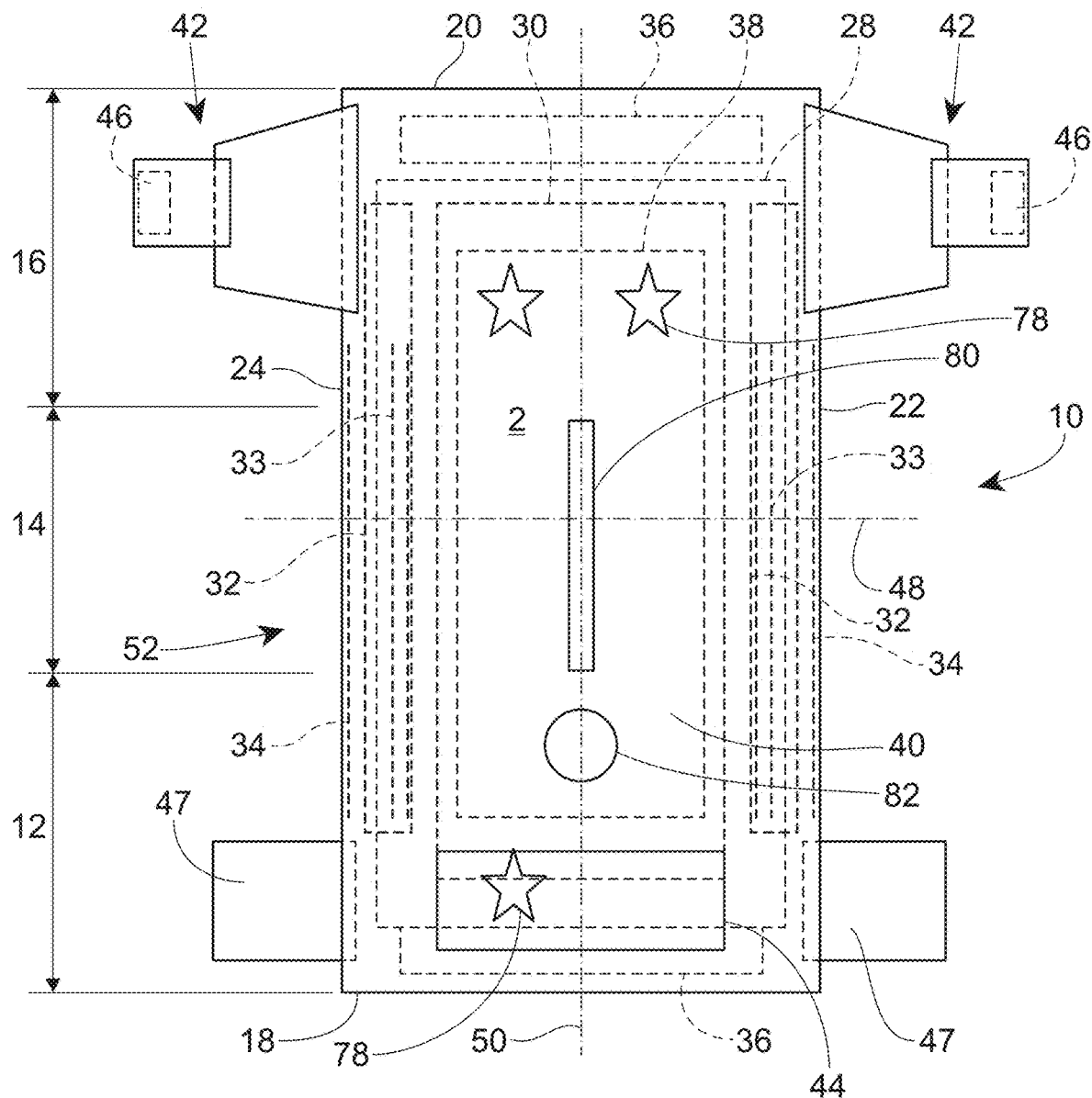
FIG. 1 is a plan view of an example absorbent article in the form of a taped diaper, garment-facing surface facing the viewer, in a flat laid-out state.
Figure 2:
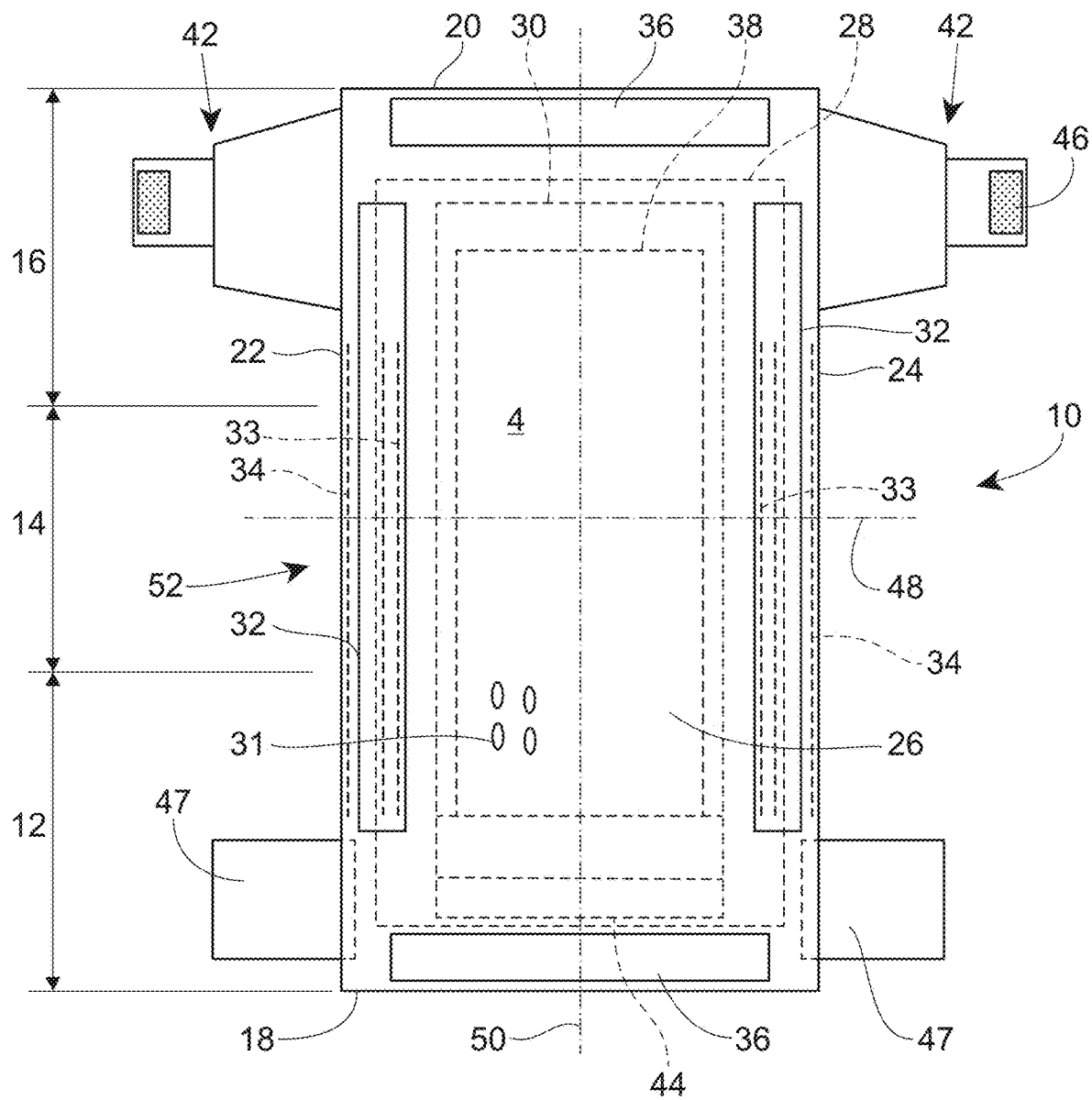
FIG. 2 is a plan view of the example absorbent article of FIG. 1, wearer-facing surface facing the viewer, in a flat laid-out state.
Figure 3:
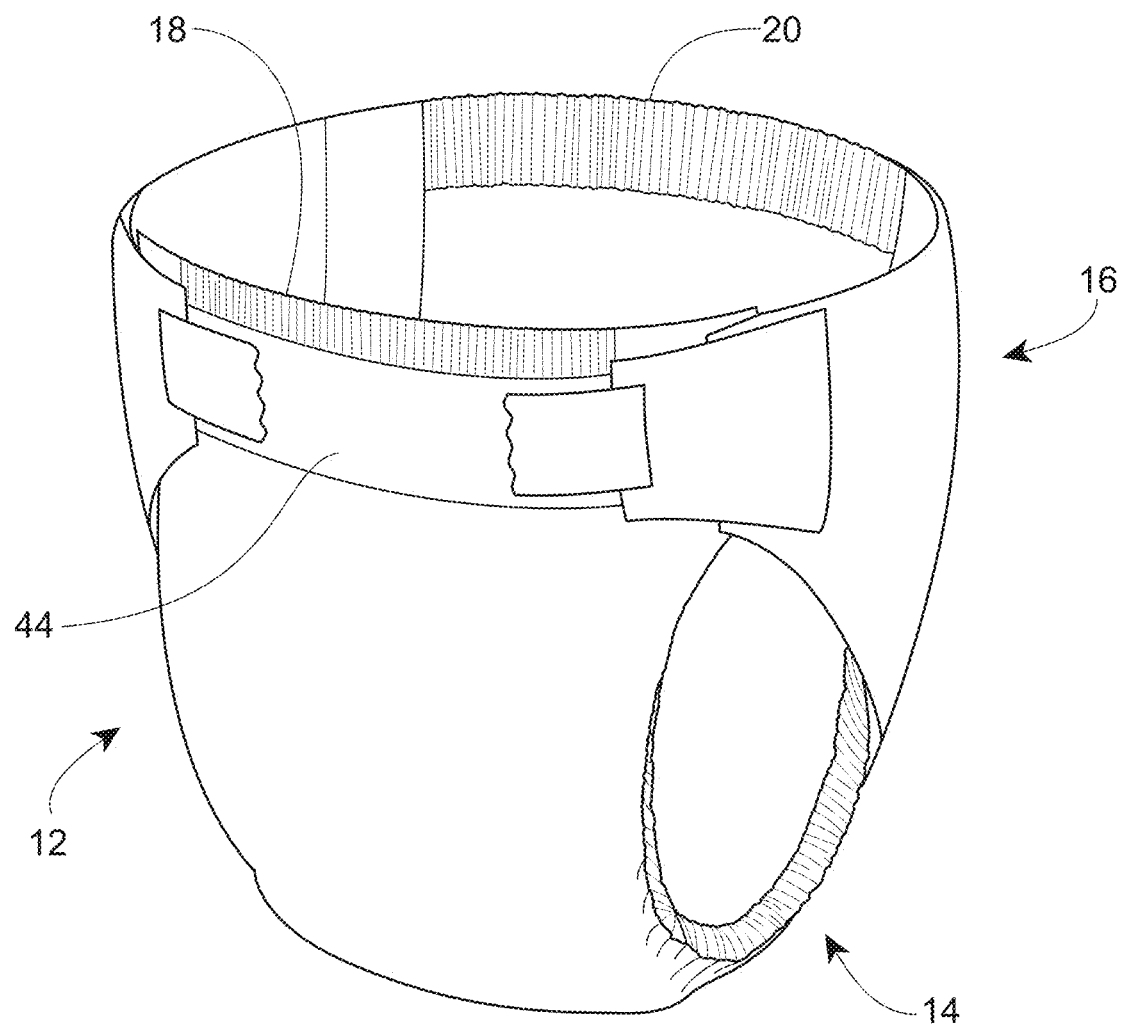
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
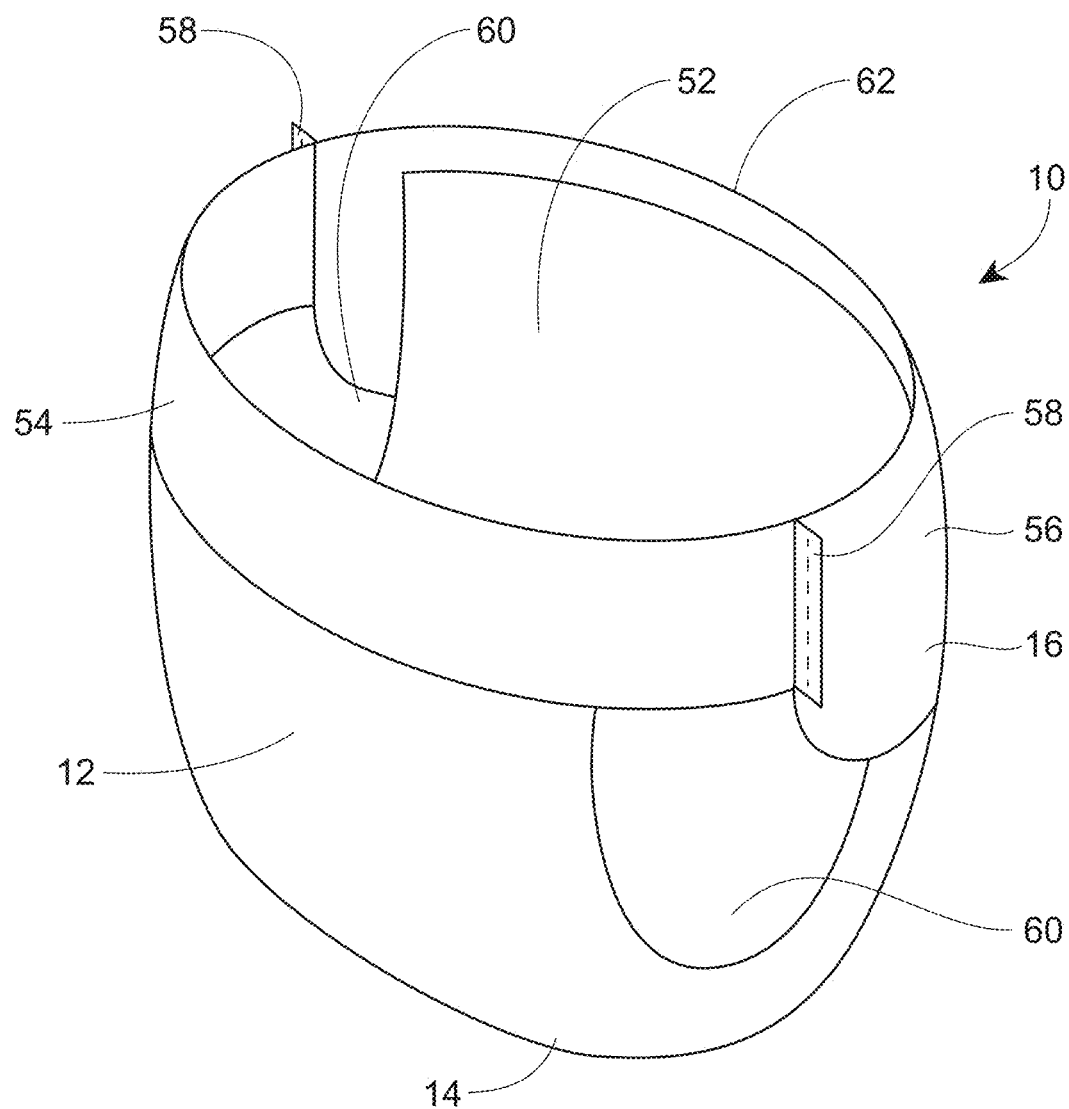
FIG. 4 is a front perspective view of an absorbent article in the form of a pant.
Figure 5:
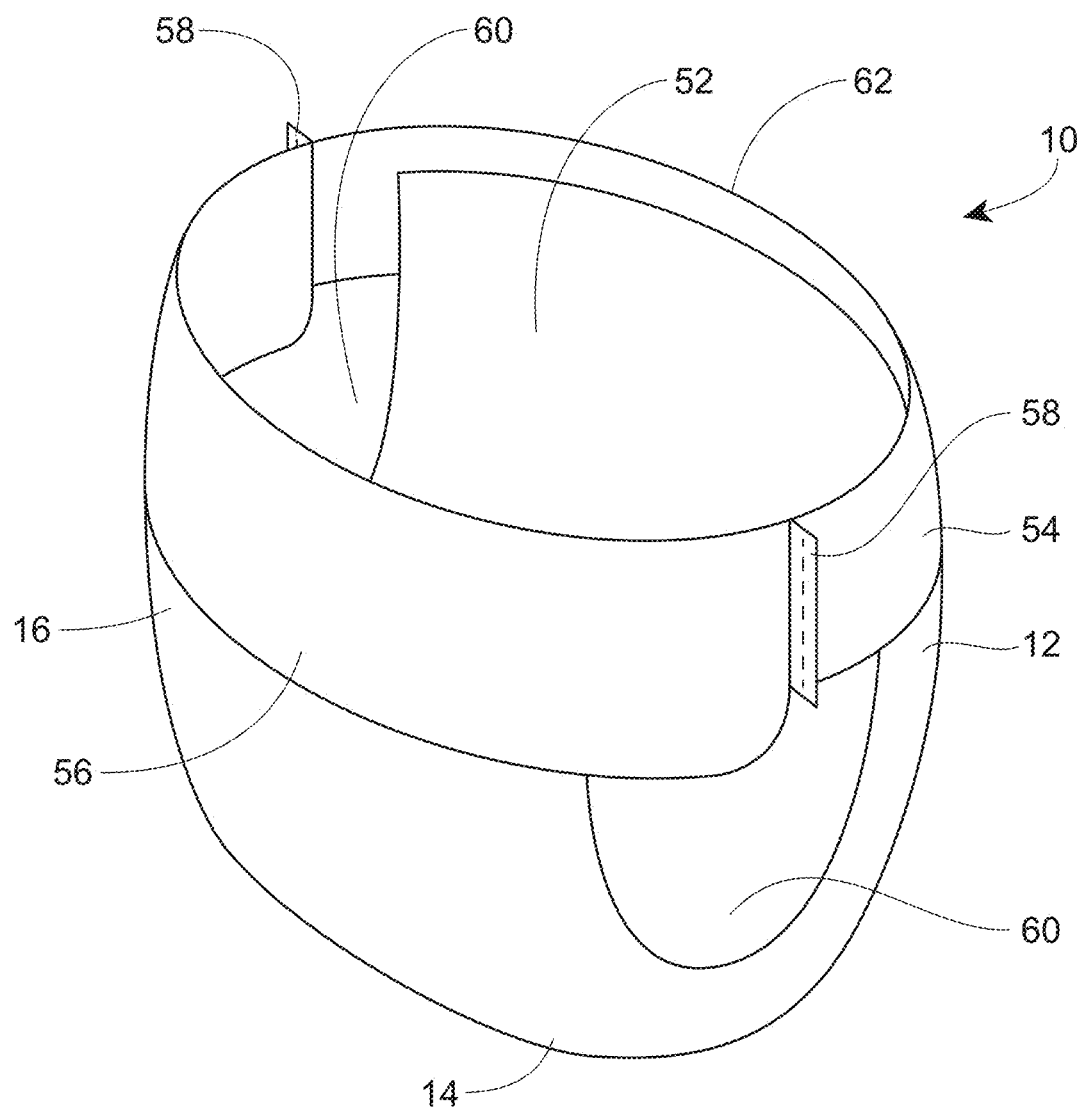
FIG. 5 is a rear perspective view of the absorbent article of FIG. 4.
Figure 6:
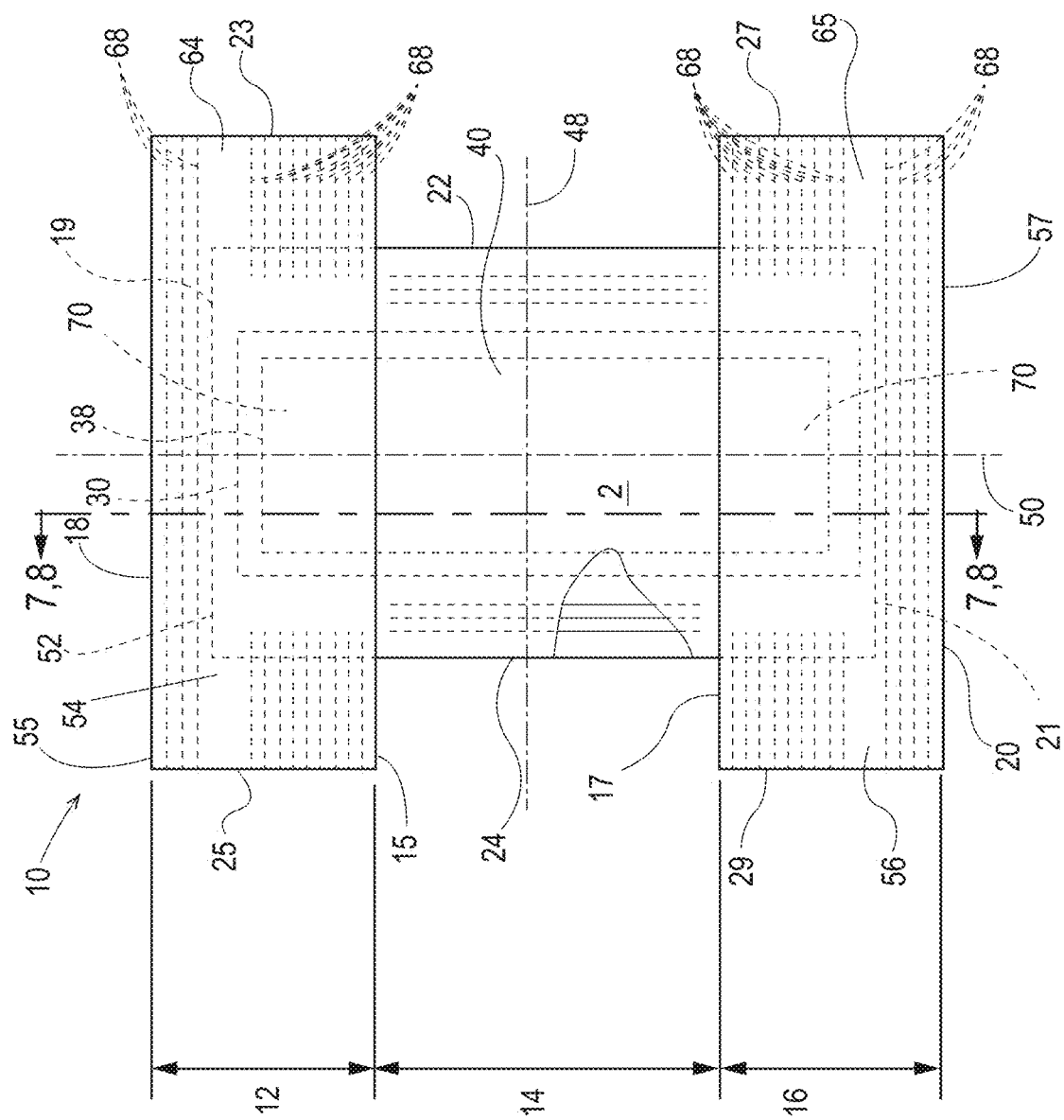
FIG. 6 is a plan view of the absorbent article of FIG. 4, laid flat, with a garment-facing surface facing the viewer.
Figure 7:
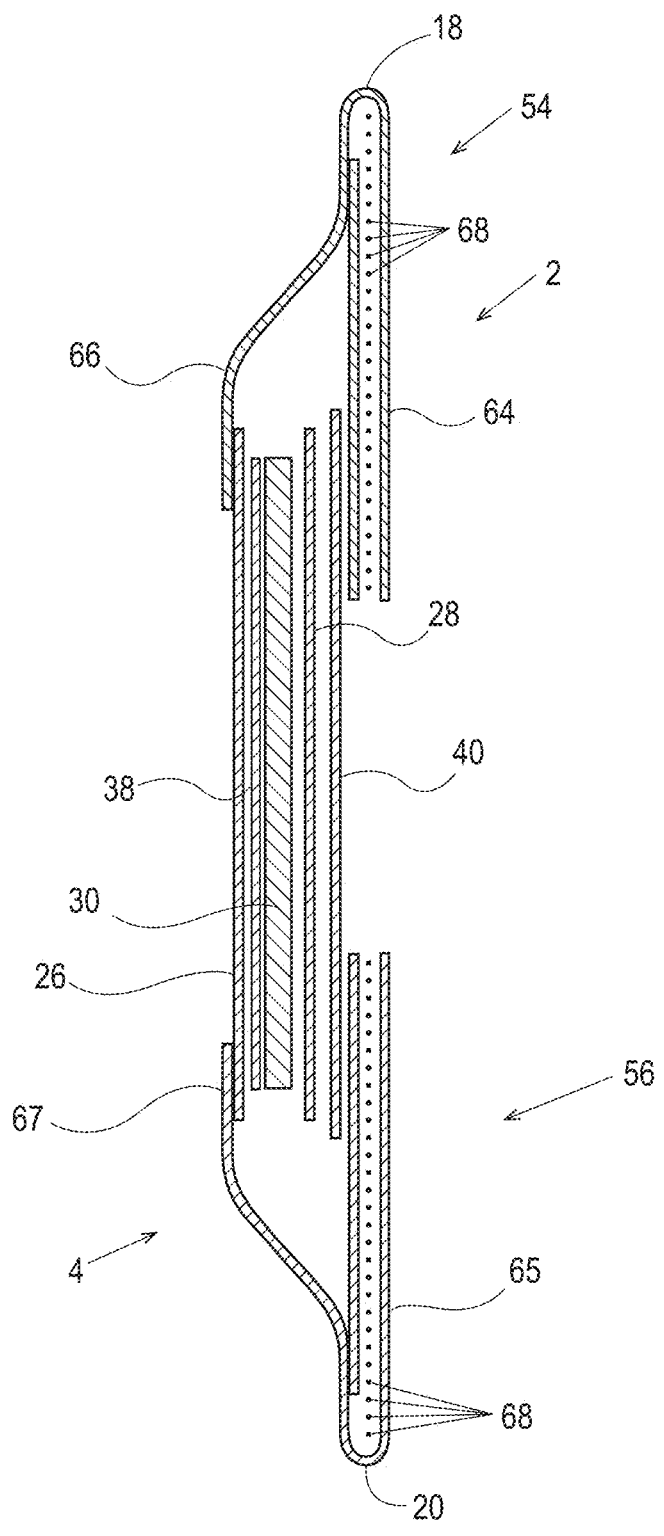
FIG. 7 is a cross-sectional view of the absorbent article taken about line 7-7 of FIG. 6.
Figure 8:
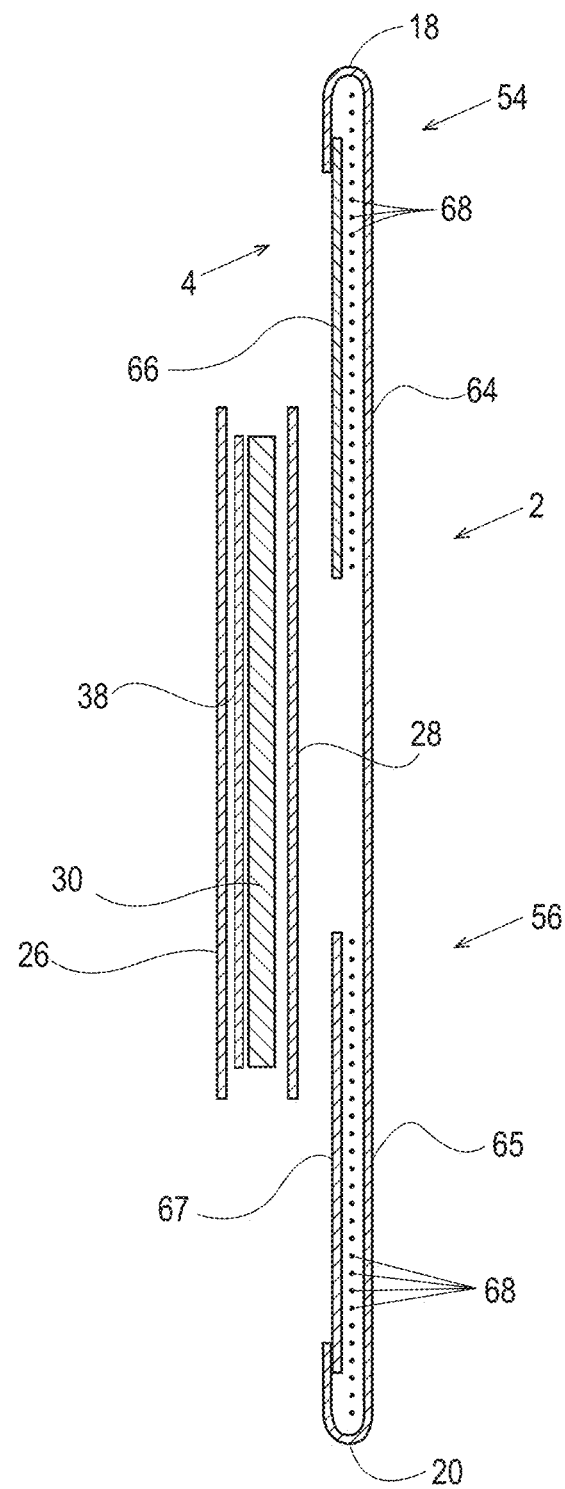
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily wastes to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily wastes may pass through the topsheet.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily wastes absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily wastes from passing through the backsheet.

Outer Cover Material

The outer cover nonwoven material (sometimes referred to as a backsheet nonwoven) 40 may comprise one or more nonwoven materials joined to the backsheet 28 and that covers the backsheet 28. The outer cover nonwoven material 40 forms at least a portion of the garment-facing surface 2 of the absorbent article 10 and effectively "covers" the backsheet 28 so that film is not present on the garment-facing surface 2. The outer cover nonwoven material 40 may comprise a bond pattern, apertures, and/or three-dimensional features.

Absorbent Core

Figure 9:
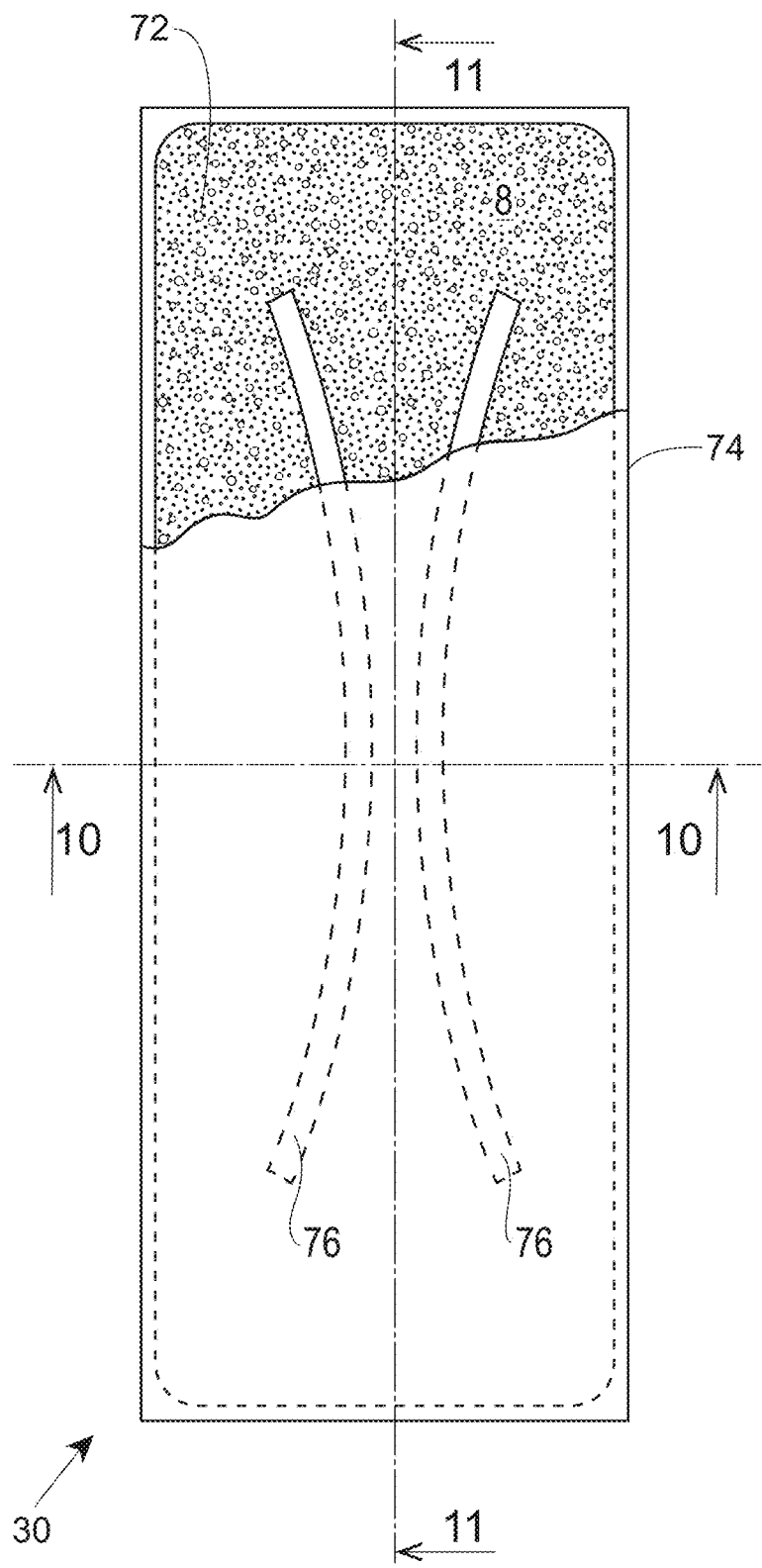
FIG. 9 is a plan view of an example absorbent core or an absorbent article.
Figures 10, 11:
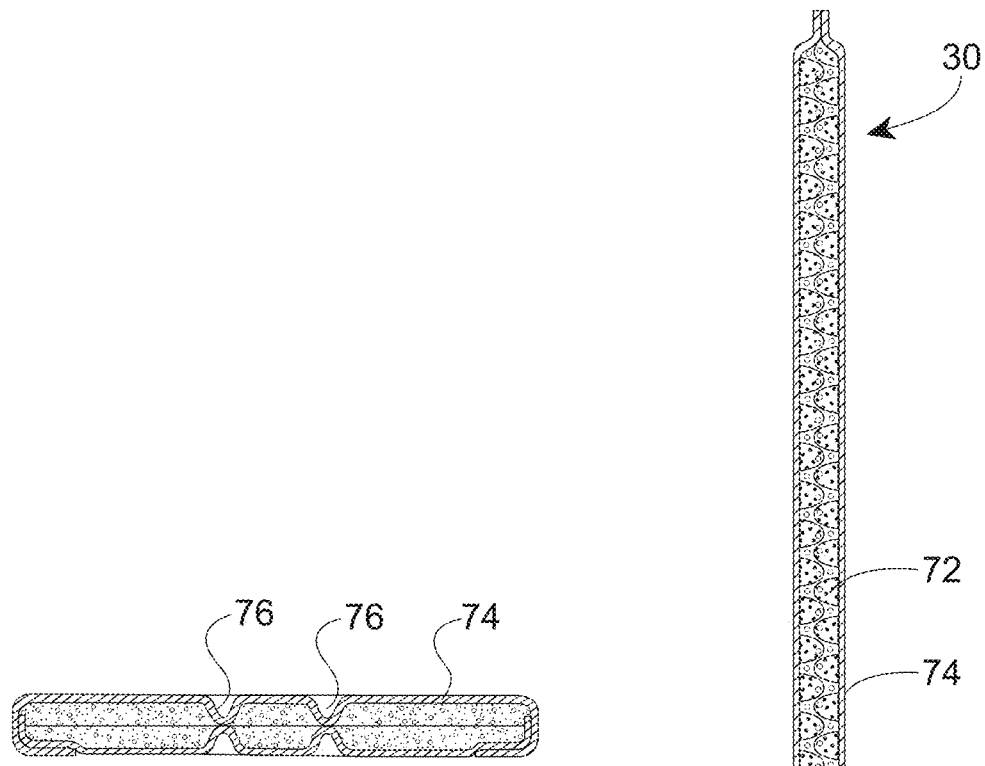
FIG. 10 is a cross-sectional view, taken about line 10-10, of the absorbent core of FIG. 9.
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body wastes approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily wastes from escaping the absorbent article 10 through the waist opening circumference. In some instances, an elastic waistband may fully surround the waist opening circumference of an absorbent article.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily wastes within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily wastes (e.g., the sensor system 82 may sense variations in temperature, humidity, presence of ammonia or urea, various vapor components of the bodily wastes (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages.

Sanitary Napkin

Figure 12:
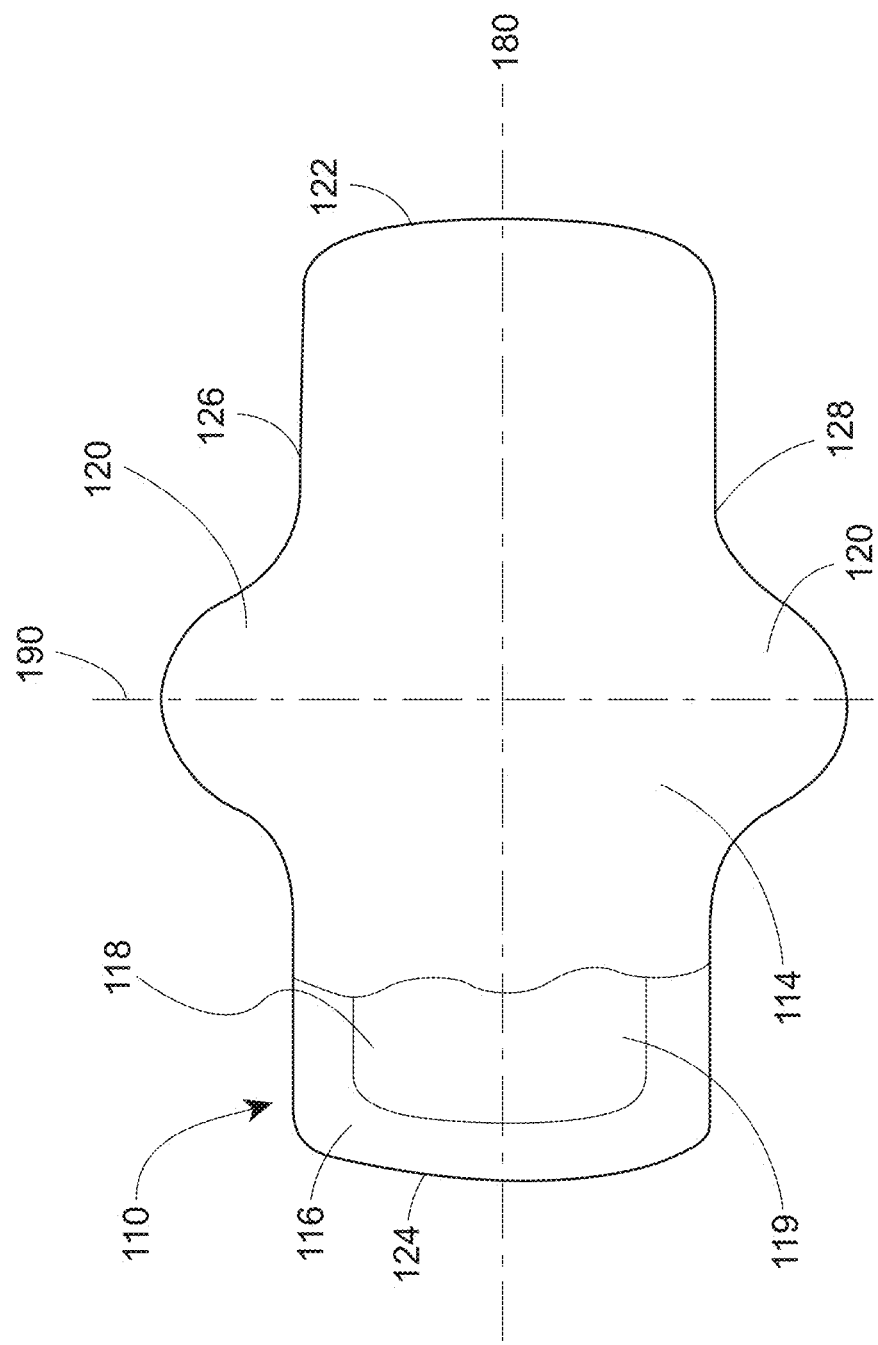
FIG. 12 is a plan view of an example absorbent article that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Acquisition Materials

Next, the acquisition materials of the present disclosure will be discussed. Referring to FIGS. 1, 2, 7, and 8, one or more acquisition materials 38 may be present at least partially intermediate the topsheet 26 and the absorbent core 30. The acquisition materials 38 may comprise one or more hydrophilic nonwoven materials that provide wicking of bodily wastes. The acquisition materials 38 may also comprise one or more hydrophobic nonwoven materials or acquisition materials that have hydrophilic and hydrophobic portions or layers. These materials may dewater the topsheet 26 and quickly acquire and store low viscosity waste or feces. The acquisition materials 38 may comprise one or more nonwoven materials. The nonwoven acquisition materials may be resin bonded materials with about 60% to about 80%, or about 70% fibers, by weight of the acquisition material, and about 20% to about 40%, or about 30% latex binder, by weight of the acquisition material. The fibers may comprise carded fibers. Acquisition materials may also comprise other nonwoven materials, cellulosic materials, high-loft nonwoven materials, spunbond high-loft nonwoven materials, and/or foams, for example. The high-loft nonwoven materials may comprise polyolefins, polyesters, and/or polyurethanes, for example. Alternative structures may comprise large diameter filaments (e.g., 0.5 mm, 0.75 mm, or even 1 mm) randomly laid down and intersecting one another at bonding points. Typically, an acquisition material 38 may have a width and length that are smaller than the width and length of the topsheet 26. The acquisition material may be a secondary topsheet in the feminine pad or sanitary napkin context. The acquisition material may have one or more channels as described above with reference to the absorbent core 30 (including the embossed version). The channels in the acquisition material may align or not align with any channels in the absorbent core 30. In some instances, a cross-linked cellulosic layer may be positioned intermediate the acquisition material and the topsheet. In other instances, the acquisition material (whether one or more layers) may be positioned intermediate the topsheet and the absorbent core.

Caliper

The acquisition materials (whether one or more layers) of the present disclosure may have a caliper in the range of about 1.5 mm to about 15 mm, about 1.8 mm to about 12 mm, about 2 mm to about 12 mm, about 1.8 mm to about 10 mm, about 2 mm to about 10 mm, about 2.5 mm to about 10 mm, about 3 mm to about 10 mm, or about 3.5 mm to about 10 mm, about 4 mm to about 9 mm, or about 4 mm to about 8 mm, specifically reciting all 0.1 mm increments within the specified ranges and all ranges formed therein or thereby. All caliper measurements are according to the Caliper Test herein.

Air Permeability

The acquisition materials (whether one or more layers) of the present disclosure may have an air permeability in the range of about 4,000 $l/m^2/s$ to about 14,000 $l/m^2/s$, about 5,000 $l/m^2/s$ to about 11,000 $l/m^2/s$, about 6,000 $l/m^2/s$ to about 11,000 $l/m^2/s$, about 6,100 $l/m^2/s$ to about 11,000 $l/m^2/s$, about 5,000 $l/m^2/s$ to about 10,000 $l/m^2/s$, about 6,000 $l/m^2/s$ to about 10,000 $l/m^2/s$, or about 6,100 $l/m^2/s$ to about 10,000 $l/m^2/s$, specifically reciting all 1 $l/m^2/s$ increments within the specified ranges and all ranges formed therein or thereby. All air permeability measurements are according to the Air Permeability Test herein.

Basis Weight

The acquisition materials (whether one or more layers) of the present disclosure may have a basis weight in the range of about 20 gsm to about 150 gsm, about 40 gsm to about 120 gsm, about 50 gsm to about 110 gsm, about 60 gsm to about 100 gsm, about 70 gsm to about 95 gsm, about 80 gsm to about 90 gsm, or about 86 gsm, specifically reciting all 0.1 gsm increments within the specified ranges and all ranges formed therein or thereby. All basis weight measurements are according to the Basis Weight Test herein.

Layers

Figure 13:
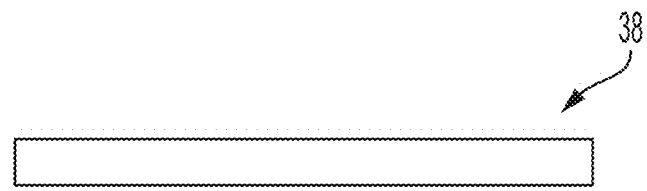
FIG. 13 is a schematic illustration of a side view of a single layer acquisition material.
Figure 14:
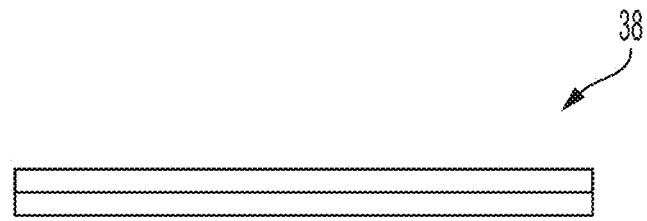
FIG. 14 is a schematic illustration of a side view of a two layer acquisition material.

The acquisition materials 38 of the present disclosure may comprise a single layer or may comprise multiple layers, such as two or three layers, for example. FIG. 13 is a schematic illustration of side view of a single layer acquisition material 38. FIG. 14 is a schematic illustration of a side view of a two layer acquisition material 38. The first layer may be joined (e.g., bonds, adhesives) to the second layer or the first layer may not be joined to the second layer. In other instances, the first layer may only be joined to the second layer in certain areas and not joined in other areas. Alternatively, the first and second layers, or portions thereof, may be joined only by physical or geometric interactions, such as by being mechanically entangled or nested, for example. If a single layer acquisition material is provided, the single layer may be homogeneous throughout its thickness and/or dimensions or may have an air permeability gradient and/or density gradient throughout its thickness. If an air permeability gradient and/or density gradient is provided, the higher air permeability side and/or the lower density side may typically face toward the wearer. If more than one layer is provided in an acquisition material, each layer may be the same or different in fiber type, composition, basis weight, air permeability, dimensions, caliper, and/or density, for example. The acquisition materials may be rectangular or may be shaped (e.g., not rectangular, such as hourglass shaped).

Three Dimensional Features

Figure 15:
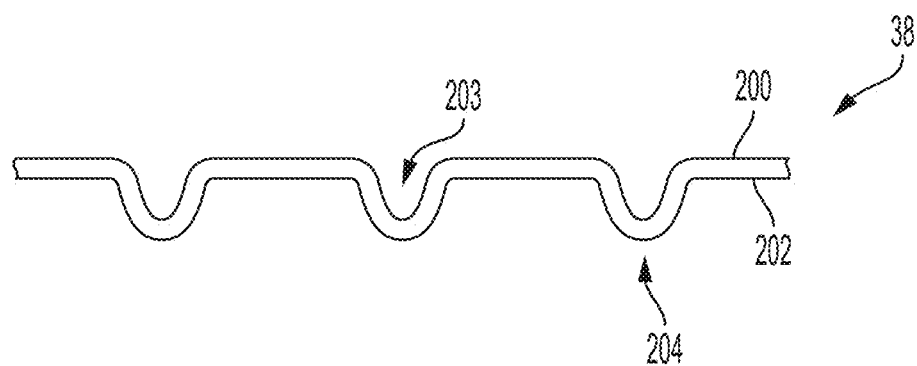
FIGS. 15-18 are schematic illustrations of side views of two layer acquisition materials comprising three-dimensional features.
Figure 16:
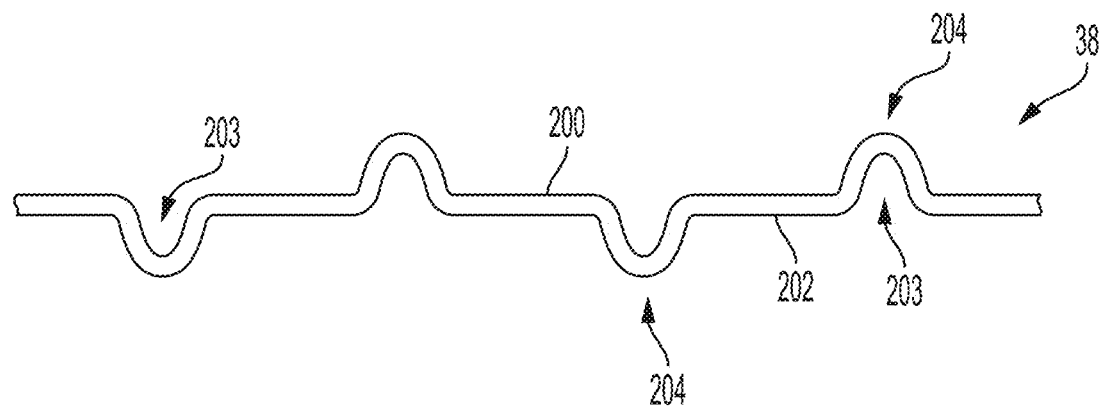

The acquisition materials may comprise three-dimensional features or be "activated" or "mechanically activated". Examples of tooling for activation or mechanical activation is illustrated in FIGS. 19-24, 26, 27, and 29-32. An example of an activated nonwoven or mechanically activated nonwoven is illustrated in FIGS. 25-28. Any suitable physical process that increases the caliper and air permeability of the material may be classified in the context of activation or mechanical activation. This may lead to more storage space for low viscosity feces or waste and further improve acquisition through a topsheet, or other layer, and into the acquisition material. FIGS. 15 and 16 are schematic illustrations of side views of acquisition materials. The acquisition material 38 may comprise a first surface 200, a second surface 202, and three-dimensional features 204 extending outwardly from the first surface 200 or the second surface 202. The three-dimensional features 204 may extend toward the absorbent core or may extend toward the topsheet when placed in an absorbent article. In some instances, some three-dimensional features may extend toward the topsheet and other three-dimensional features may extend towards the absorbent core (see FIG. 16). In such an instance, the three-dimensional features 204 may extend outwardly from the first surface 200 and extend outwardly from the second surface 202. FIGS. 15 and 16 illustrate two layer acquisition materials in a "nested" structure, but it will be understood that only one layer may be used while still retaining the same structure of the three-dimensional features 204. Void spaces 203 are created in the acquisition materials 38 via the three-dimensional features 204. These void spaces 203 aid in acquisition and storage of low viscosity feces or waste, thereby inhibiting blowouts and waste on skin. The first surface 200 or the second surface 202 of the acquisition materials 38 of FIGS. 15 and 16 may face the topsheet of an absorbent article. Low viscosity feces or waste may enter the void spaces through the first layer or the second layer owing to the open porosity and high air permeability of the layers.

At least some of, a majority of, or all of the three-dimensional features may have an area in the range of about 10 $mm^2$ to about 200 $mm^2$, about 20 $mm^2$ to about 150 $mm^2$, about 30 $mm^2$ to about 100 $mm^2$, or about 40 $mm^2$ to about 80 $mm^2$, specifically reciting all 1 $mm^2$ increments within the specified ranges and all ranges formed therein or thereby. At least some of, a majority of, or all of the three-dimensional features may have a largest dimension in the range of about 2 mm to about 20 mm, about 4 mm to about 10 mm, or about 4 mm to about 8 mm, specifically reciting all 1 mm increments within the specified ranges and all ranges formed therein or thereby. The "largest dimension" means the longest measurable length through an X-Y plane at a base of a three-dimensional feature taken at its widest point or across its largest perimeter (whether the perimeter is continuous or discontinuous). The X-Y plane extends in the same direction as the first surface 200 and the second surface 202. The three-dimensional features may have any suitable X-Y plane shape, such as hearts, circles, ovals, octagons, rectangles, elongate bars, or squares, for example. In some instances, all of the three-dimensional elements may be the same shape (accounting for manufacturing tolerances) in an acquisition material. In other instances, more than one shape of three-dimensional features may be provided in an acquisition material.

Figure 17:
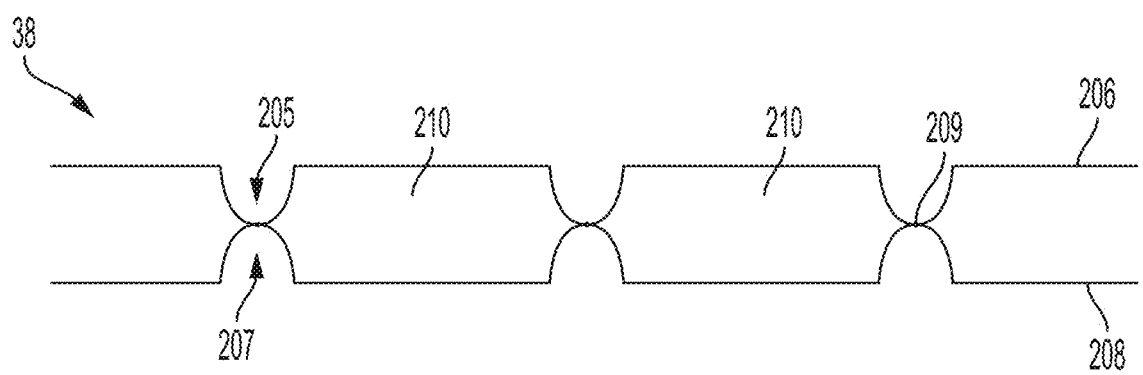

FIG. 17 is a schematic illustration of a side view of a two layer acquisition material 38 having a first layer 206 and a second layer 208. The first layer 206 comprises three-dimensional features 205 and the second layer comprises three-dimensional features 207. Tips of the three-dimensional features 205 may be joined (e.g., bonded or glued)

209 to tips of the three-dimensional features 207 to create large void spaces 210 in the acquisition material 38. In other instances, the tips may not be joined together. These large void spaces 210 may aid in acquisition and storage of low viscosity feces or waste, thereby inhibiting blowouts or waste on skin. Void spaces may also be created in the three-dimensional features 205, 207. Low viscosity feces or waste may enter the void spaces through the first layer or the second layer owing to their open porosity and high air permeability.

Figure 18:
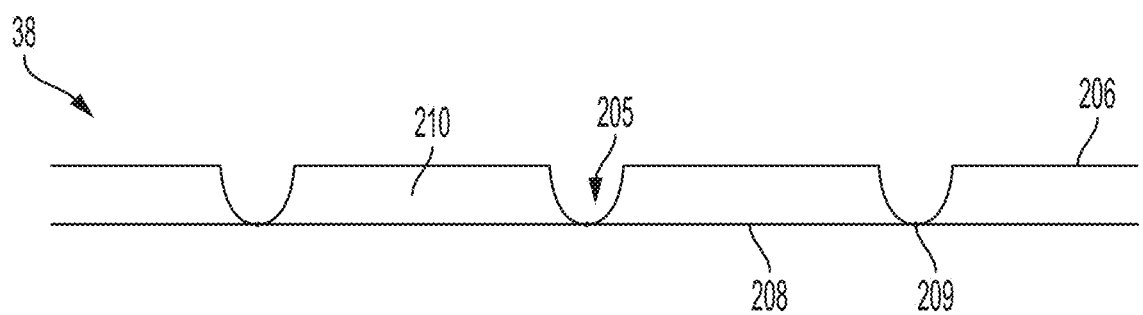

FIG. 18 is a schematic illustration of a side view of a two layer acquisition material 38 having a first layer 206 and a second layer 208. The first layer 206 comprises three-dimensional features 205 and the second layer 208 may be generally planar. Tips of the three-dimensional features 205 of the first layer 206 may be joined (e.g., bonded or glued) 209 to the planer second layer 208 to create large void spaces 210 in the acquisition material 38. In other instances, the tips may not be joined to the second layer 208. These void spaces 210 may aid in acquisition and storage of low viscosity feces or waste, thereby inhibiting blowouts and waste on skin. Void spaces may also be created in the three-dimensional features 205. The generally planar second layer 208 may face the topsheet or may face the absorbent core in an absorbent article. Low viscosity feces or waste may enter the void spaces through the first layer or the second layer owing to their open porosity and high air permeability.

Figure 21:
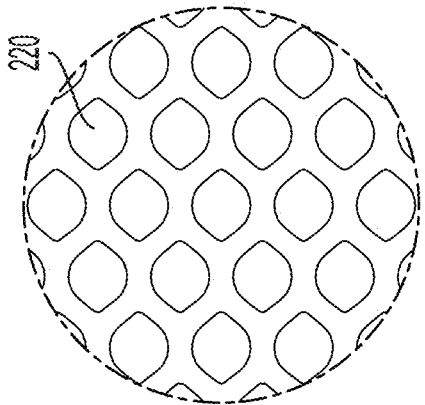
FIG. 21 is detail view of FIG. 20.
Figure 19:
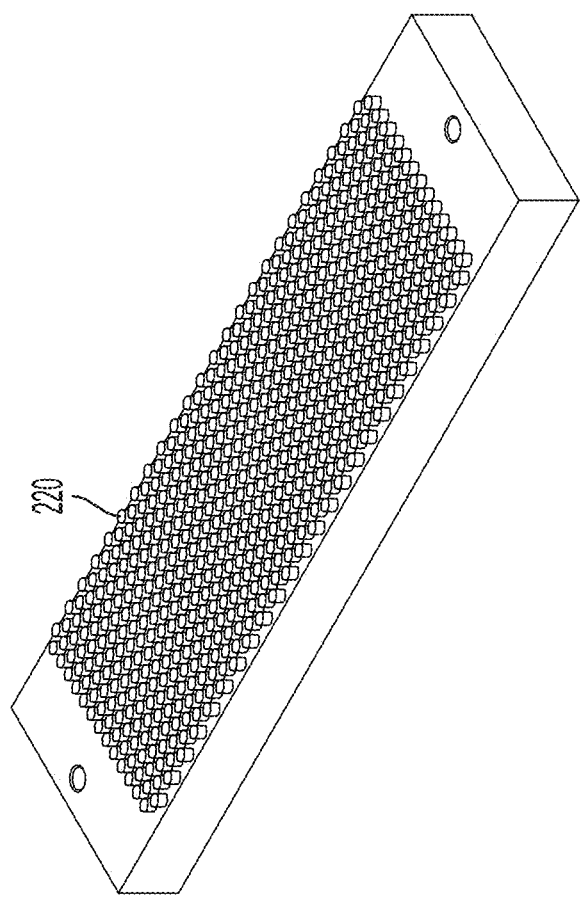
FIG. 19 is a perspective view of a plate comprising male embossing or mechanical intermeshing tooling.
Figure 20:
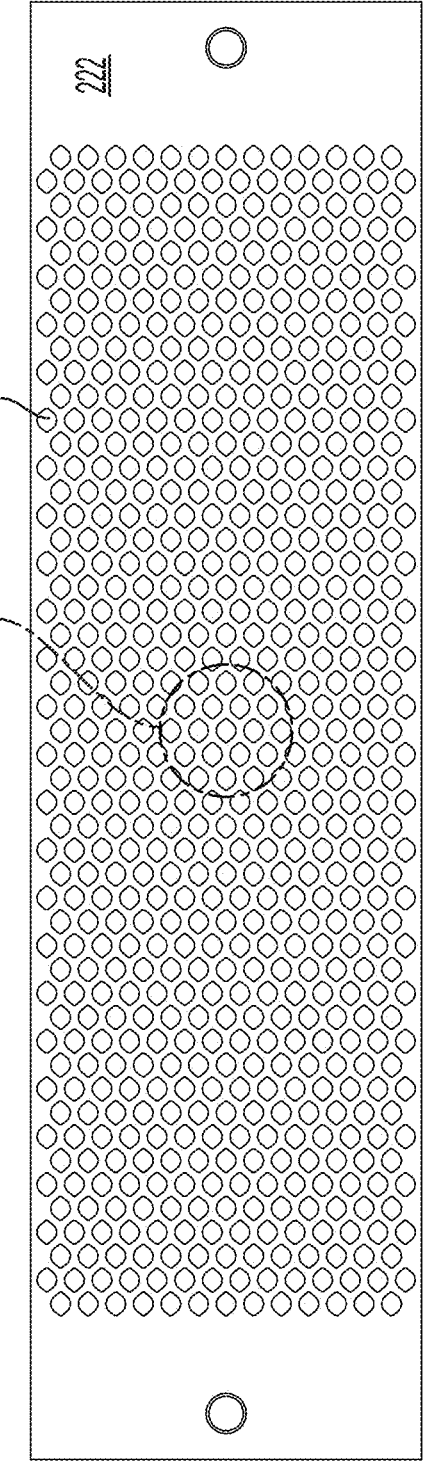
FIG. 20 is a top view of the plate comprising the male embossing or mechanical intermeshing tooling of FIG. 19.

As an example, the three-dimensional features discussed herein may be created via male female embossing and/or mechanical intermeshing. FIGS. 19-21 illustrate example male embossing or mechanical intermeshing tooling that may be used with the female embossing or mechanical intermeshing tooling of FIGS. 22-24 to create a pattern of three-dimensional features in an acquisition material. The male-female embossing or mechanical intermeshing may be used to create void spaces in and activate or mechanically activate an acquisition material. One or more layers may be embossed or mechanical intermeshed together (see FIGS. 15 and 16) or single layers may be embossed or mechanical intermeshed separately. If single layers are embossed or mechanical intermeshed separately, they may optionally be joined with other embossed or mechanical intermeshed single layers to create, for example, the structure illustrated in FIG. 17. Also, if single layers are embossed or mechanical intermeshed separately, they may be joined with a generally planar layer to create the structure of FIG. 18.

Figure 24:
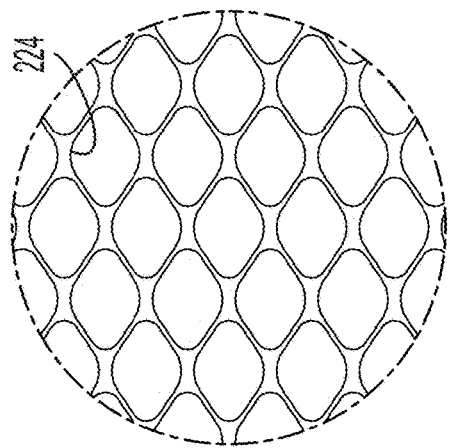
FIG. 24 is detail view of FIG. 23.
Figure 22:
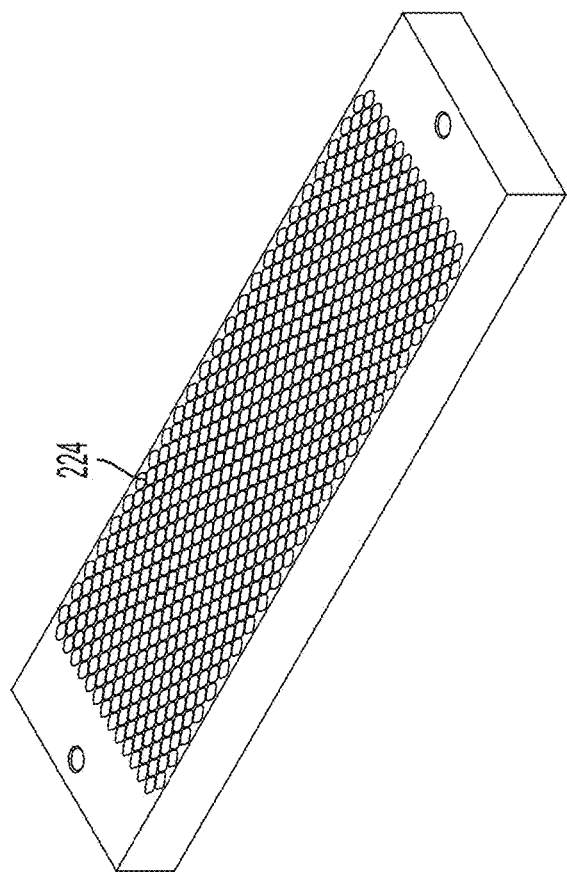
FIG. 22 is a perspective view of a plate comprising female embossing or mechanical intermeshing tooling.
Figure 23:
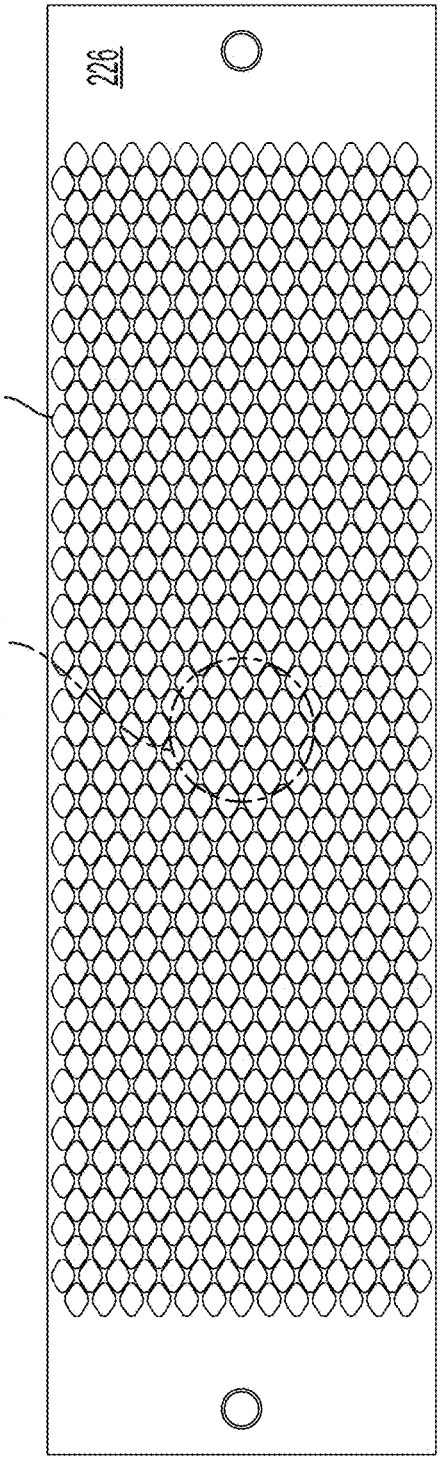
FIG. 23 is a top view of the plate comprising the female embossing or mechanical intermeshing tooling of FIG. 22.

FIG. 19 is a perspective view of a plate comprising male embossing or mechanical intermeshing tooling. FIG. 20 is a top view of the plate comprising the male embossing or mechanical intermeshing tooling of FIG. 19. FIG. 21 is detail view of FIG. 20. A plurality of projections 220 may extend outwardly from a surface 222 of the male embossing or mechanical intermeshing tooling. The projections 220 may have the illustrated shape, a cylindrical shape, or other suitable shape. Although the male embossing or mechanical intermeshing tooling is illustrated on a plate, it will be understood that such tooling may also be provided on an outer surface of a cylindrical roll. FIG. 22 is a perspective view of a plate comprising female embossing or mechanical intermeshing tooling. FIG. 23 is a top view of the plate comprising the female embossing or mechanical intermeshing tooling of FIG. 22. FIG. 24 is detail view of FIG. 23. A plurality of recesses 224 may extend inwardly from a surface 226 of the female embossing or mechanical intermeshing tooling. Although the female embossing or mechanical intermeshing tooling is illustrated on a plate, it will be understood that such tooling may also be provided on an outer surface of a roll. The male embossing or mechanical intermeshing tooling works in conjunction with the female embossing or mechanical intermeshing tooling to create the three-dimensional features in an acquisition material. The projections 220 of the male embossing or mechanical intermeshing tooling may partially, or fully engage the recesses 224 of the female embossing or mechanical intermeshing tooling to create the three-dimensional features in an acquisition material. The amount that the projections 220 of the male embossing or mechanical intermeshing tooling engage the recesses 224 of the female embossing or mechanical intermeshing tooling is known as the depth of engagement or "DOE". The depth of engagement may be varied depending on the desired three-dimensional features. A smaller depth of engagement produces shorter or smaller three-dimensional features in an acquisition material, while a larger depth of the engagement produces larger or higher three-dimensional features in an acquisition material. The recesses 224 may be slightly larger than the projections 220 to allow the projections 220 to fit at least partially, or fully, within the recesses 224. The recesses 224 and the projections 220 may both have the same shape or may have similar shapes. The patterns of projections 220 and recesses 224 may be varied and may contain areas without projections or recesses.

Figure 25:
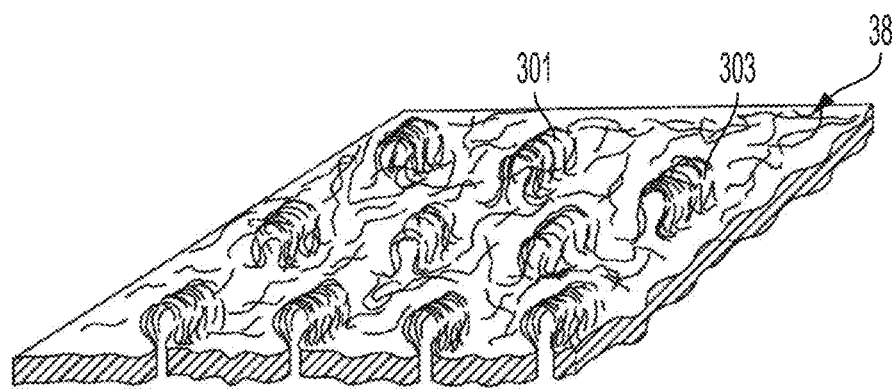
FIG. 25 is a perspective view of an acquisition material with three-dimensional features.

FIG. 25 is a perspective view of an example acquisition material 38 of the present disclosure with three-dimensional features 301. The acquisition material 38 may comprise one or more layers and may take on one or more of the two layer configurations illustrated in FIGS. 15-18, for example. In a single layer configuration, the three-dimensional features 301 may face toward the topsheet or toward the absorbent core when positioned within an absorbent article. Although tears 303 in the three-dimensional features 301 are illustrated in FIG. 25, tears may not always be present in the three-dimensional features 301 depending on the depth of engagement of the tooling, as described below with respect to FIG. 26.

Figure 26:
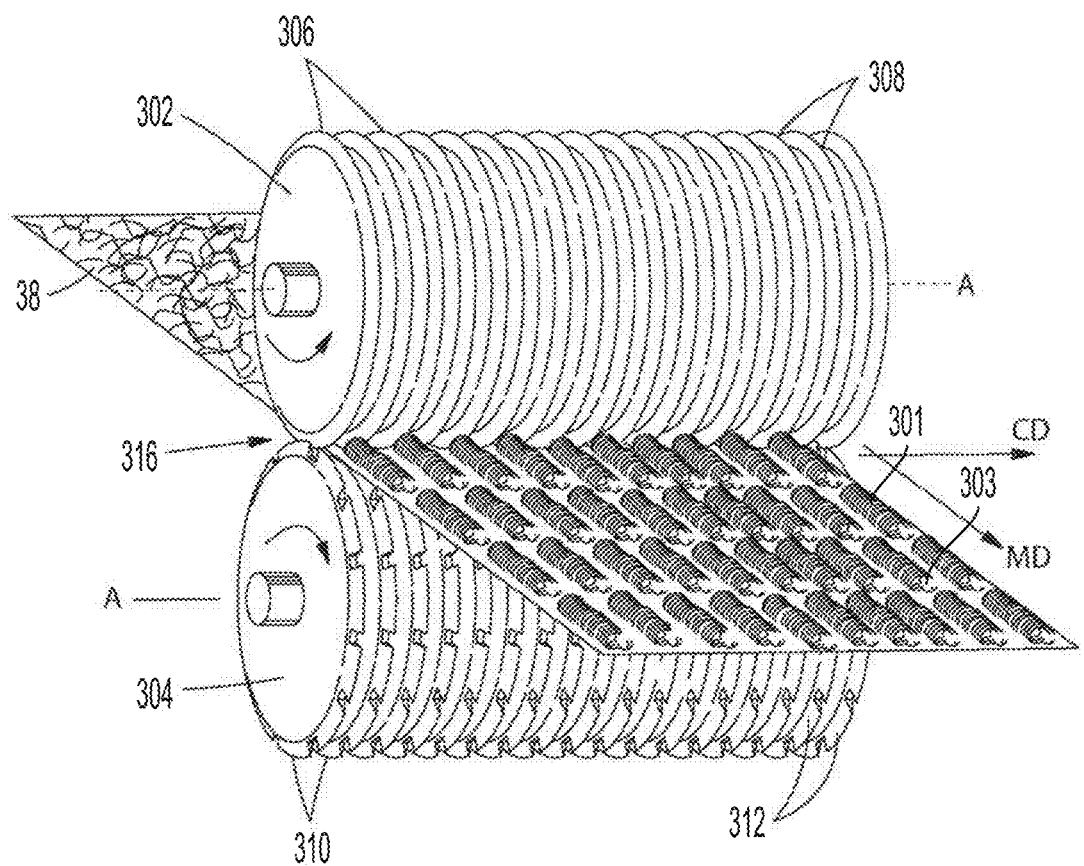
FIG. 26 illustrates a process of creating the acquisition material of FIG. 25.

The acquisition material 38 of FIG. 25 may be produced by the process and tooling illustrated in FIG. 26. A pair of intermeshing rollers 302 and 304 may form a nip 316 through which a one or more layer acquisition material 38 may be conveyed to create the three-dimensional features 301 in the acquisition material. The intermeshing roller 302 may comprise a plurality of ridges 306 and a plurality of grooves 308 and may rotate about axis, A, in the direction shown by the arrow. The second intermeshing roller 304 may comprise a plurality of circumferentially spaced teeth 310 and a plurality of grooves 312 and may rotate about axis, A, in the direction shown by the arrow. The plurality of ridges 306 of the first roller 302 may at least partially, or fully, engage the plurality of grooves 312 of the second roller 304. The plurality of circumferentially spaced teeth 310 of the second roller 304 may at least partially, or fully, engage the plurality of grooves 306 of the first roller 302. The distance that the ridges 306 and the circumferentially spaced teeth 310 engage the grooves 312 and 308, respectively, is the depth of engagement or DOE. To create larger or higher three-dimensional features 301 in the acquisition material, a greater depth of engagement is used. To create smaller or shorter three-dimensional features 301 in the acquisition material, a smaller depth of engagement is used. Typically, a larger depth of engagement is used if tears 303 in the three-dimensional elements 301 are desired and a smaller depth of engagement is used if tears 303 in the three-dimensional elements 301 are not desired. The tears 303 may provide easy access for low viscosity feces or waste to void space created by the three-dimensional features 301, thereby reducing blowouts and waste on skin. The machine direction, MD, and the cross-machine direction, CD, are illustrated in FIG. 26.

Figure 27:
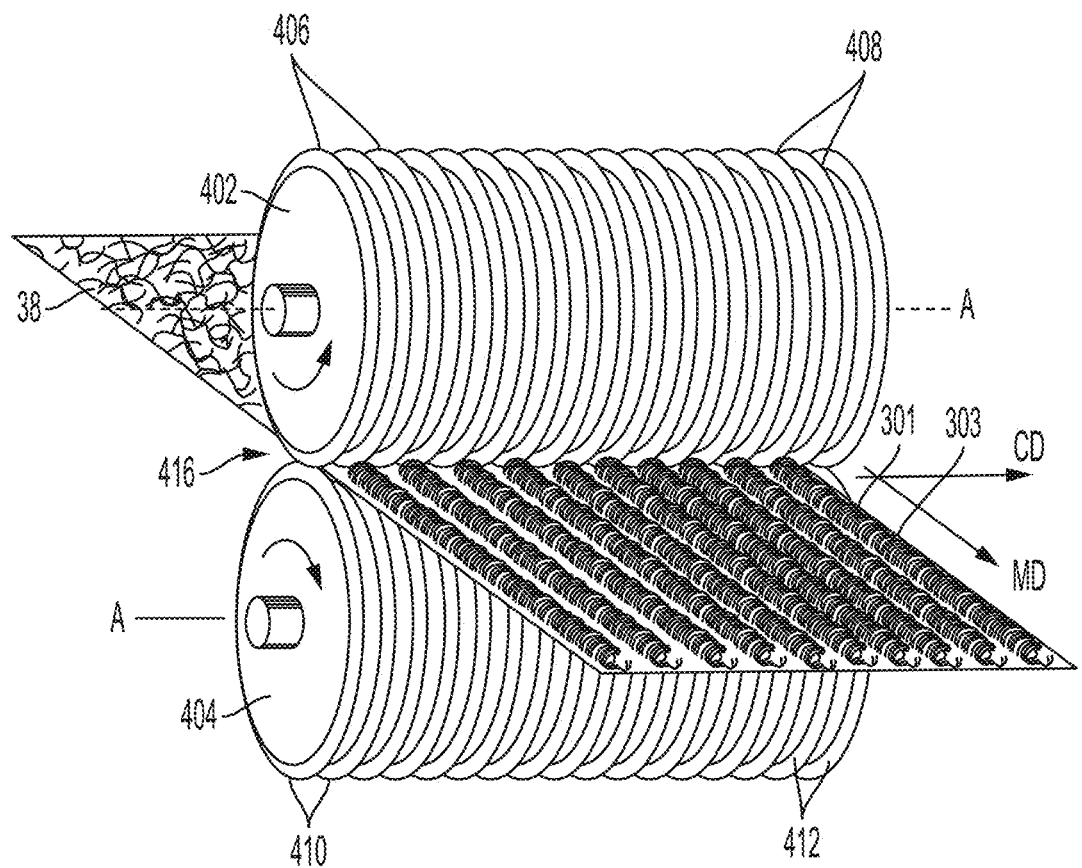
FIG. 27 illustrates a process of creating an acquisition material.

The acquisition material 38 shown in FIG. 27 may be produced by the process illustrated in FIG. 27. A pair of intermeshing rollers 402 and 404 may form a nip 416 through which a one or more layer acquisition material 38 may be conveyed to create the three-dimensional features 401 in the acquisition material. The intermeshing roller 402 may comprise a plurality of ridges 406 and a plurality of grooves 408 and may rotate about axis, A, in the direction shown by the arrow. The second intermeshing roller 404 may comprise a plurality of ridges 410 and a plurality of grooves 412 and may rotate about axis, A, in the direction shown by the arrow. The plurality of ridges 406 of the first roller 402 may at least partially, or fully, engage the plurality of grooves 412 of the second roller 404. The plurality of ridges 410 of the second roller 404 may at least partially, or fully, engage the plurality of grooves 406 of the first roller 402. The distance that the ridges 406 and the ridges 410 engage the grooves 412 and 408, respectively, is the depth of engagement. Three-dimensional features are created both on a first side of the acquisition material 38 and a second side of the acquisition material by the intermeshing rollers 402 and 404. To create larger or higher three-dimensional features 401 in the acquisition material, a greater depth of engagement is used. To create smaller or shorter three-dimensional features 401 in the acquisition material, a smaller depth of engagement is used. Typically, a larger depth of engagement is used if tears 403 in the three-dimensional elements 401 are desired and a smaller depth of engagement is used if tears 403 in the three-dimensional elements 401 are not desired. The tears 403 may provide easy access for low viscosity feces or waste to void space created by the three-dimensional features 401, thereby reducing blowouts and waste on skin. The machine direction, MD, and the cross-machine direction, CD, are illustrated in FIG. 27.

Figure 28:
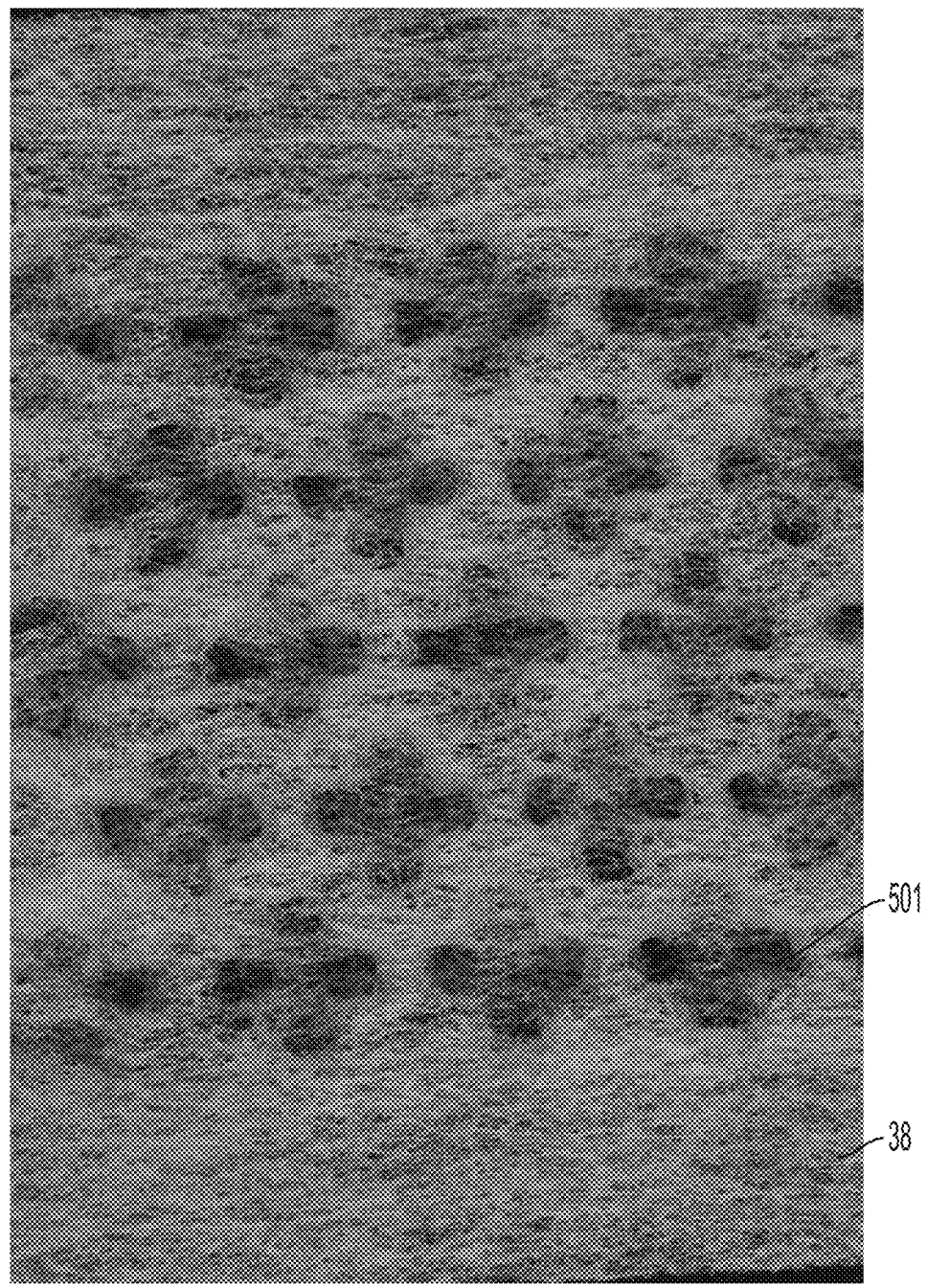
FIG. 28 is a photograph of an example acquisition material with three-dimensional features.
Figure 29:
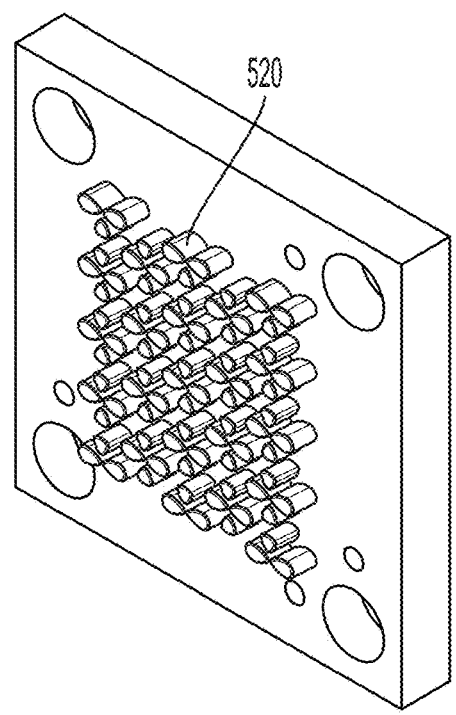
FIG. 29 is a perspective view of a plate comprising male embossing or mechanical intermeshing tooling.
Figure 30:
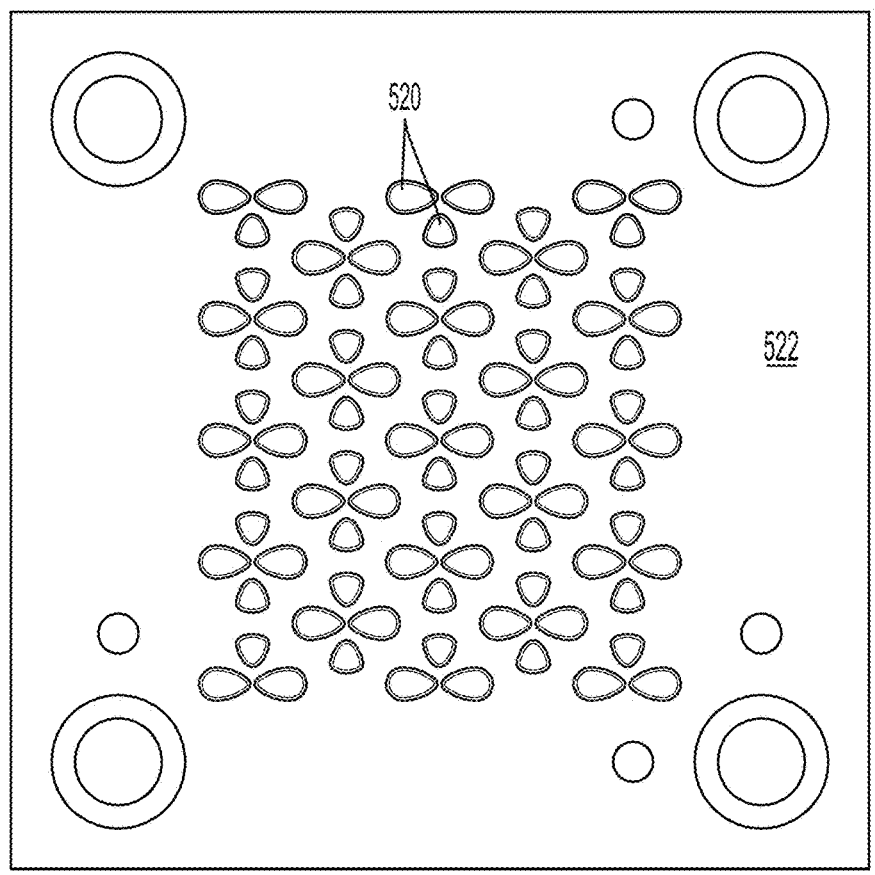
FIG. 30 is a top view of the plate comprising the male embossing or mechanical intermeshing tooling of FIG. 29.

As an example, the three-dimensional features discussed herein may be created via male female embossing and/or mechanical intermeshing. FIG. 28 an example acquisition material created by the tooling illustrated in FIGS. 29-32. FIGS. 29 and 30 illustrate example male embossing or mechanical intermeshing tooling that may be used with the female embossing or mechanical intermeshing tooling of FIGS. 31 and 32 to create a pattern of three-dimensional features in an acquisition material. The male-female embossing or mechanical intermeshing may be used to create void spaces in and activate or mechanically activate an acquisition material. One or more layers may be embossed or mechanical intermeshed together (see e.g., FIGS. 15 and 16) or single layers may be embossed or mechanical intermeshed separately. If single layers are embossed or mechanical intermeshed separately, they may optionally be joined with other embossed or mechanical intermeshed single layers to create, for example, the structure illustrated in FIG. 17. Also, if single layers are embossed or mechanical intermeshed separately, they may be joined with a generally planar layer to create the structure of FIG. 18.

Figure 31:
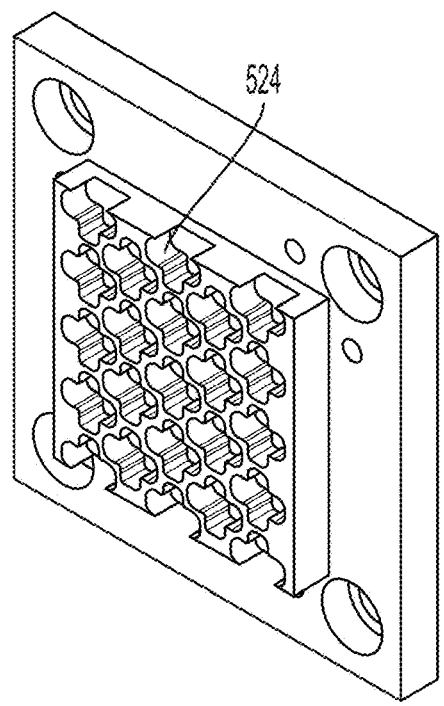
FIG. 31 is a perspective view of a plate comprising female embossing or mechanical intermeshing tooling.
Figure 32:
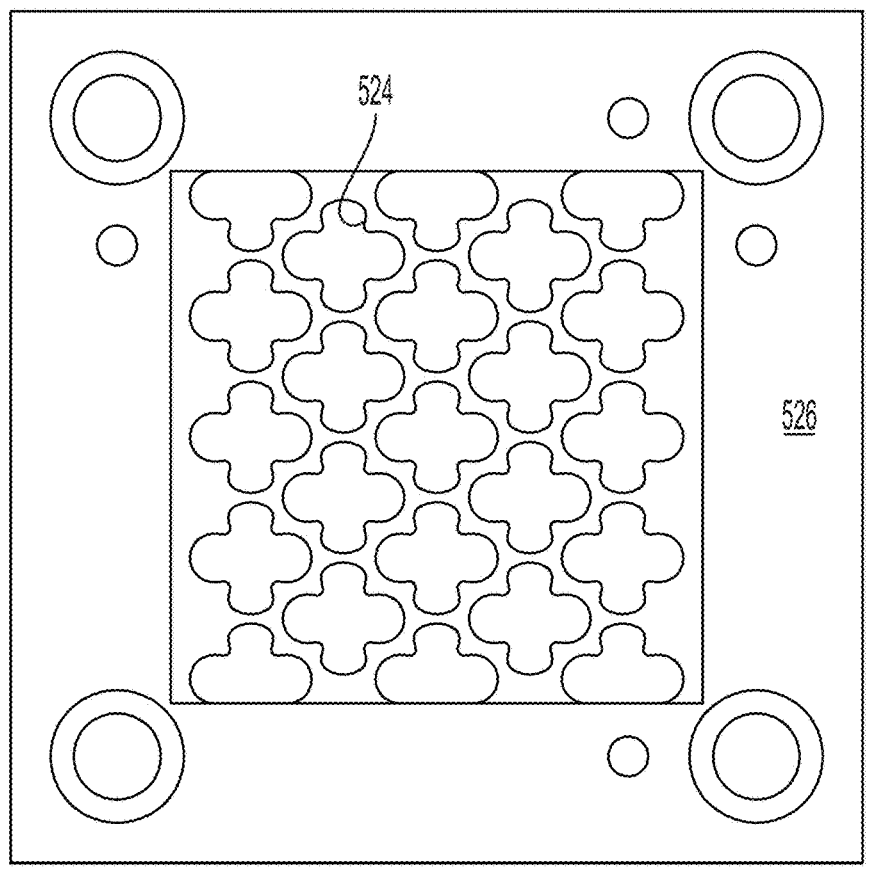
FIG. 32 is a top view of the plate comprising the female embossing or mechanical intermeshing tooling of FIG. 31.

FIG. 29 is a perspective view of a plate comprising male embossing or mechanical intermeshing tooling. FIG. 30 is a top view of the plate comprising the male embossing or mechanical intermeshing tooling of FIG. 29. A plurality of projections 520 may extend outwardly from a surface 522 of the male embossing or mechanical intermeshing tooling. The projections 520 may have the illustrated shape forming a clover pattern. Although the male embossing or mechanical intermeshing tooling is illustrated on a plate, it will be understood that such tooling may also be provided on an outer surface of a cylindrical roll. FIG. 31 is a perspective view of a plate comprising female embossing or mechanical intermeshing tooling. FIG. 32 is a top view of the plate comprising the female embossing or mechanical intermeshing tooling of FIG. 31. A plurality of recesses 524 may extend inwardly from a surface 526 of the female embossing or mechanical intermeshing tooling. Although the female embossing or mechanical intermeshing tooling is illustrated on a plate, it will be understood that such tooling may also be provided on an outer surface of a roll. The male embossing or mechanical intermeshing tooling works in conjunction with the female embossing or mechanical intermeshing tooling to create the three-dimensional features in an acquisition material. The projections 520 of the male embossing or mechanical intermeshing tooling may partially, or fully engage the recesses 524 of the female embossing or mechanical intermeshing tooling to create the three-dimensional features in an acquisition material. The amount that the projections 520 of the male embossing or mechanical intermeshing tooling engage the recesses 524 of the female embossing or mechanical intermeshing tooling is known as the depth of engagement or "DOE". The depth of engagement may be varied depending on the desired three-dimensional features. A smaller depth of engagement produces shorter or smaller three-dimensional features in an acquisition material, while a larger depth of the engagement produces larger or higher three-dimensional features in an acquisition material. The recesses 524 may be slightly larger than the projections 520 to allow the projections 520 to fit at least partially within the recesses 524. The recesses 524 and the projections 520 that engage each other may both have the same shape or may have similar shapes. The patterns of projections 520 and recesses 524 may be varied and may contain areas without projections or recesses.

Some example processes to create the three-dimensional features in acquisition materials have been disclosed herein. These processes create high-caliper, high air permeability acquisition materials. Other processes to achieve the same or similar results comprise penetrating the acquisition material with three-dimensional pins, compressing the acquisition material in a three-dimensional die, or stretching the acquisition materials homogeneously or non-homogeneously, for example. In any of the processes, heat may be applied to the acquisition materials during activation or three-dimensional feature creation to at least partially "set" the three-dimensional shape and allow them to resist subsequent compression. This resistance to compression is helpful when packaged under pressure and during wear to maintain the high caliper and high air permeability of the acquisition materials.

Apertured Topsheet

Topsheets having apertures 31 (see FIG. 2) may be used in combination with the acquisition materials of the present disclosure to form a low viscosity feces or waist acquisition system or laminate. The topsheets may be joined, bonded, glued, or otherwise attached to at least portions of the acquisition materials. In some instances, the topsheets may only be joined, bonded, glued, or otherwise attached to the acquisition materials in certain regions, while other regions remain unattached (but may still be in contact). FIG. 2 only illustrates the apertures 31 in a portion of the topsheet 26, but it will be understood that the apertures may extend throughout an area of the topsheet 26. The topsheets may comprise one or more layers, such as two layers. In an instance, a wearer-facing layer may be hydrophobic and a garment-facing layer may be hydrophilic. In another instance, the wearer-facing layer may be more hydrophobic than the garment-facing layer, but both may be hydrophilic. In order for the topsheets to be able to pass low viscosity feces or waste to the acquisition materials, the topsheets typically should have a certain size of apertures and the overall topsheet should have a certain Percent Effective Aperture Area. The apertures may have a size in the range of about 1 mm$^2$ to about 10 mm$^2$, about 1 mm$^2$ to about 8 mm$^2$, about 2 mm$^2$ to about 6 mm$^2$, or about 3 mm$^2$ to about 6 mm$^2$, specifically reciting all 0.1 mm$^2$ increments within the specified ranges and all ranges formed therein or thereby, according to the Percent Effective Area Test. The topsheets may have a Percent Effective Area in the range of about 5% to about 40%, about 8% to about 35%, about 10% to about 30%, about 12% to about 25%, or about 15% to about 25%, specifically reciting all 0.1% increments within the specified ranges and all ranges formed therein or thereby, according to the Percent Effective Area Test. Generally, topsheets with greater Percent Effective Area allow more low viscosity feces or waste to reach the acquisition materials disclosed herein, thereby reducing blowouts and waste on skin. Topsheets with lower Percent Effective Areas may become a limiting factor in how much low viscosity feces or waste reaches, and is subsequently acquired and stored by, the acquisition materials.

Example

Trans-topsheet capacity ("TTSC") is the measure of the amount of low viscosity feces or waste that can reach, and be stored in, an absorbent structure comprising an apertured topsheet and an acquisition material positioned beneath the apertured topsheet. It has been found that a TTSC of at least about 1.8 g/in$^2$, at least about 1.9 g/in$^2$ or at least about 2.0 g/in$^2$ is generally suitable to provide significant benefits to wearers compared to currently marketed absorbent articles. The acquisition material tested is a resin bonded material with about 70% fibers, by weight of the acquisition material, and about 30% latex binder, by weight of the acquisition material. The fibers are carded fibers. Each layer is 43 gsm. The properties of each of the samples are detailed in Chart 1.

CHART 1

| Material Details | # of Layers | Caliper (mm) | Air Perm (l/m2/s) | TTSC (g/in2) |
|---|---|---|---|---|
| Sample 1-Related Art: Acquisition Material (43 gsm per layer)-Currently Marketed as a two layer acquisition material of U.S. Pampers Cruisers, no three-dimensional features | 1<br>2 | 0.77<br>1.3 | 8000<br>5200 | 0.6<br>0.8 |
| Sample 2-Present Disclosure: Acquisition Material (43 gsm per layer) with pattern created by tooling of FIGS. 19-24, at 0.09 DOE | 1<br>Three-dimensional features facing toward the topsheet | 1.8 | 9600 | 1.9 |
| Sample 3-Present Disclosure: Acquisition Material (43 gsm per layer) with pattern created by tooling of FIGS. 19-24, at 0.09 DOE | 2<br>Three-dimensional features of both layers nested and facing toward the topsheet pattern up | 3.5 | 6100 | 2.1 |
| Sample 4: Acquisition Material (43 gsm per layer) made by the equipment of FIG. 27, at 0.095 DOE | 1<br>Three-dimensional features facing toward the topsheet and other three-dimensional features facing toward the absorbent core | 0.7 | 13800 | 0.9 |
| Sample 5-Present Disclosure: Acquisition Material (43 gsm per layer) large clover pattern made by the equipment of FIGS. 29-32 | 2<br>Three-dimensional features facing towards the topsheet | 4.1 | 6500 | 2.2 |

Samples 2, 3, and 5 show examples of acquisition materials of the present disclosure with certain air permeability and caliper that achieve a TTSC of at least about 1.8 g/in$^2$, and provide the benefits of the acquisition materials of present disclosure. Samples 1 and 4 are examples of acquisition materials that did not have a TTSC of at least about 1.8 g/in$^2$ and, therefore, do not provide all of the benefits of the acquisition materials of the present disclosure. Sample 1 is related art. Sample 4 is an embodiment that was tested that did not achieve a suitable TTSC.

TTSC may be in the range of about 1.8 g/in$^2$ to about 4 g/in$^2$, about 1.9 g/in$^2$ to about 4 g/in$^2$, about 2 g/in$^2$ to about 3.5 g/in$^2$, about 2 g/in$^2$ to about 3 g/in$^2$, for example. TTSC is measured according to the Trans-topsheet Capacity Test herein.

Competitive Acquisition Materials:

Applicants have tested three competitive acquisition materials as set forth in Chart 2 below according to the Air Permeability Test and the Caliper Test herein. The competitive data shows that existing high air permeability acquisition materials are also quite thin, as compared to the acquisition materials of the present disclosure. The extreme thinness (low caliper) of the competitive art samples provide extremely low capacity for viscous bodily waste even if coupled with a topsheet having the Percent Effective Area values described herein (but the competitive absorbent articles do not have apertured topsheets meeting this criteria). Two of the samples also lack the air permeability for viscous bodily waste to even penetrate the structure adequately, even if they had sufficient capacity. These acquisition materials are not designed, or configured in a diaper, to address the viscous bodily waste needs of younger infants.

CHART 2

| Competitive Product | # of Layers | Caliper (mm) | Air Perm (l/m2/s) |
|---|---|---|---|
| Goon Premium, Size 4 (also called Goon Angel); Batch Lot: 20180904 C4141001627; (Commercially available in China) | 1 | 0.3 | 8686 |
| Lelch, Size 4; Batch Lot: 20181114 MM20211113 (Commercially available in China) | 1 | 0.2 | 5109 |
| Merries, Size 4; Batch Lot: S011528 2018061; (Commercially available in China) | 1 | 0.7 | 5577 |

Test Methods
Basis Weight Test

Basis weight of the materials described herein may be determined by several available techniques, but a simple representative technique involves taking an absorbent article or other consumer product, removing any elastic which may be present and stretching the absorbent article or other consumer product to its full length. A punch die having an area of 45.6 cm$^2$ is then used to cut a piece of the material being measured from the approximate center of the absorbent article or other consumer product in a location which avoids to the greatest extent possible any adhesive which may be used to fasten the material to any other layers which may be present and removing the material from other layers (using cryogenic spray, such as Cyto-Freeze, Control Company, Houston, Tex., if needed). The sample is then weighed and dividing by the area of the punch die yields the basis weight of the material. Results are reported as a mean of 5 samples to the nearest 0.1 gram per square meter (gsm).

Percent Effective Area Test

Effective aperture dimensions, percent effective area and inter-aperture distance measurements are obtained from aperture specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif., or equivalent). The scanner is interfaced with a computer running an image analysis program (a suitable program is ImageJ v. 1.47, National Institute of Health, USA, or equivalent). The specimen images are distance calibrated against an acquired image of a ruler certified by NIST. The aperture specimen is backed with a black glass tile (P/N 11-0050-30, available from HunterLab, Reston, Va., or equivalent) prior to acquiring the image. The resulting grayscale image is then converted to a binary image via a threshold gray-level value, enabling the separation of open aperture regions from specimen material regions, and these regions analyzed using the image analysis program. All testing is performed in a conditioned room maintained at about 23±2° C. and about 50±2% relative humidity.

Sample Preparation:

To obtain a specimen, the absorbent article is taped to a rigid flat surface in a planar configuration. Any leg elastics present may be cut to facilitate laying the article flat. The outer boundary of the region lying above the absorbent core of the article is identified and marked on the apertured layer. The specimen of apertured layer is removed from the underlying layers of the article by cutting around the outer perimeter of the article with a razor blade. The apertured layer specimen is carefully removed such that its longitudinal and lateral extension is maintained to avoid distortion of the apertures. A cryogenic spray (such as Cyto-Freeze, Control Company, Houston Tex., or equivalent) can be used to remove the specimen from the underlying layers if necessary. Five replicate specimens obtained from five substantially similar articles are prepared for analysis. An apertured substrate raw material is prepared for testing by extending or activating it under the same process conditions, and to the same extent, as it would be for use on the absorbent article. The samples are conditioned at about 23° C.±2° C. and about 50%±2% relative humidity for 2 hours prior to testing.

Image Acquisition:

The ruler is placed on the scanner bed such that it is oriented parallel to the sides of the scanner glass. An image of the ruler (the calibration image) is acquired in reflectance mode at a resolution of 6400 dpi (approximately 252 pixels per mm) and in 8-bit grayscale. The calibration image is saved as an uncompressed TIFF format file. After obtaining the calibration image, the ruler is removed from the scanner glass and all specimens are scanned under the same scanning conditions. An apertured specimen is placed onto the center of the scanner bed, lying flat, with the outward facing surface of the specimen facing the scanner's glass surface. The corners and edges of the specimen are secured such that its original longitudinal and lateral extension, as on the article prior to removal, is restored. The specimen is oriented such that the machine direction (MD) and cross direction (CD) of the apertured specimen layer are aligned parallel with and perpendicular to the sides of the scanner's glass surface and that the resulting specimen image has the MD vertically running from top to bottom. The black glass tile is placed on top of the specimen, the scanner lid is closed, and a scanned image of the entire specimen is acquired. The specimen image is save as an uncompressed TIFF format file. The remaining four replicate specimens are scanned and saved in like fashion. Prior to analysis, all specimen images are cropped to the largest rectangular field of view contained within the apertured region which had been located above the absorbent core of the article.

Percent Effective Area and Percent Effective Aperture Area Calculation:

The calibration image file is opened in the image analysis program and a linear distance calibration is performed using the imaged ruler. This distance calibration scale is applied to all subsequent specimen images prior to analysis. A specimen image is in the image analysis program and the distance scale is set using the distance calibration. The 8-bit grayscale image is then converted to a binary image (with "zero" or "black" corresponding to the aperture regions) in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined.

Each of the discrete aperture regions is analyzed using the image analysis program. All individual aperture areas are measured and recorded to the nearest 0.01 mm$^2$, including partial apertures along the edges of the image. Concurrently, the equivalent diameter of each aperture area is calculated from the measured area and recorded to the nearest 0.1 mm. Any apertures with an area less than 0.3 mm$^2$ are defined as "non-effective" and discarded. The remaining apertures, so-called "effective" aperture areas that include whole and partial apertures, are summed in area. This sum is then divided by the total area included in the image. This value is multiplied by 100% and reported as the effective area to the nearest 0.01%. The arithmetic mean of the equivalent areas among all "effective" apertures is calculated and recorded as the characteristic aperture equivalent area of the specimen.

The remaining four specimen images are analyzed similarly. The arithmetic mean percent effective area values for the five replicate specimens is calculated and reported to the nearest 0.01%. Similarly, the arithmetic mean of the characteristic aperture equivalent area values for the five replicate specimens is calculated and reported to the nearest 0.1 mm$^2$.

Caliper Test

The Caliper of a substrate is determined using the Caliper Test method. In the Caliper Test method, two flat, parallel surfaces are used to apply unidirectional pressure to both sides of a substrate specimen, and the resulting separation between the parallel surfaces is measured. All measurements are performed in a laboratory maintained at 23±2 ° C. and 50±2% relative humidity and test specimens are conditioned in this environment for at least 2 hours prior to testing.

Two parallel surfaces at least 1.0 in$^2$ (6.5 cm$^2$) in area are oriented horizontally. Five nominally equivalent rectangular specimens are taken from a substrate sample such that the length and width of each specimen is greater than the largest dimension of smaller of the parallel surfaces. (For example, if a flat, circular foot is brought against a large granite base, the length and width of each specimen is larger than the diameter of the circle such that the specimen can fill the entire gap between the circular foot and granite base during the measurement.) A specimen is placed between the two parallel surfaces so as to completely cover the smaller parallel surface. The parallel surfaced are brought to together at a rate of 3.0±1.0 mm/s until a pressure of 0.07 psi (0.48 kPa) is achieved, and the separation between the plates is measured and recorded to the nearest 0.1 mm within 5 seconds. The arithmetic mean of the plate separation of the individual replicate specimens is calculated and reported as the Caliper of the substrate in units of millimeters (mm) to the nearest 0.1 mm.

One suitable example of apparatus for use in the Caliper Method is a Mitutoyo Digimatic Series 543 ID-C digital indicator (Mitutoyo America Corp., Aurora, Ill., USA), or equivalent, fitted with a circular flat "foot" at the end of the moving shaft of the indicator gauge. The indicator is mounted on a horizontal granite base such that the shaft of the indicator gauge is oriented vertically and the plane of the circular foot is parallel to the granite base. The circular foot is sized and weighted such that the gravitational force associated with the mass of the foot and the indicator shaft together divided by the area of the circular foot constitutes 0.07 psi of downward pressure from the circular foot on the granite base. Specimens at least as large as the circular foot are analyzed between the circular foot and granite base.

Air Permeability Test

The Air Permeability of a substrate is determined according to INDA/EDANA Nonwovens Standard Procedures NWSP 070.1.R0 (15) making use of a Textest FX3300 (Textest Instruments, Schwerzenbach, Switzerland) air permeability tester or equivalent. A test head with area 20 cm$^2$ is used, and while a fixed pressure of 125 Pa is maintained across the substrate, air flow is measured in liters per square meter per second (l/m$^2$/s). Five nominally equivalent specimens of a sample substrate are analyzed in this way, and the air permeability of each is recorded in l/m$^2$/s to three significant figures. The arithmetic mean of the individual specimen results is calculated and reported as the Air Permeability in units l/m$^2$/s to the closest 1 l/m$^2$/s.

Trans-Topsheet Capacity Test

Figure 33:
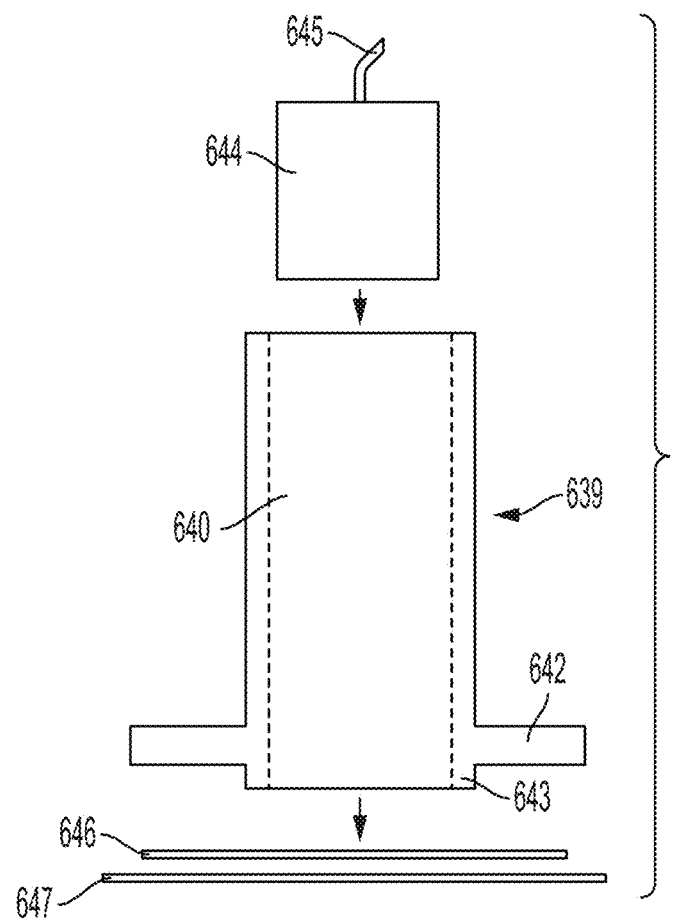
FIG. 33 is equipment used in the Trans-topsheet Capacity Test.

Trans-topsheet capacity is measured by the following test. The apparatus 639 used for this measurement is illustrated in FIG. 33.

A hollow stainless steel cylinder 640 mounted on a plate 642 is provided. The stainless steel cylinder 640 has a height of 7.5 centimeters (2.95 inches), an inside diameter of 5.08 centimeters (2.00 inches) and an outside diameter of 6.3 centimeters (2.48 inches). The bottom of the cylinder 640 extends below the plate 642 a distance of 3.5 millimeters, and has a lip with an annular thickness of 3.5 millimeters. The lip 643 prevents the fecal material analog from leaking outside the designated test area of the sample.

Also provided is a weight 644 of 100.6 grams. The weight 444 is also cylindrically shaped and has a diameter of 5.08 centimeters (2.0 inches), so that the weight 644 fits tightly within the cylinder 640 but may freely slide throughout the hole in the cylinder 640. This arrangement provides a pressure of 49.57 kilogram-force per square meter (0.071 pounds per square inch) and a test area of 3.142 square inches. If desired, the weight 644 may have a handle 645 to allow it to be easily inserted into and removed from the cylinder 640.

Figure 34:
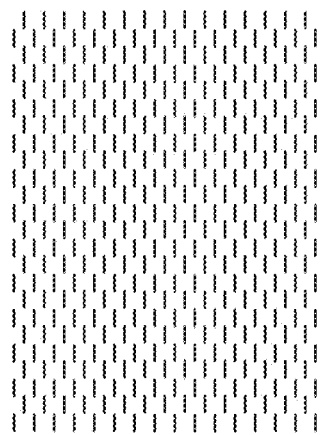
FIG. 34 is an overbond pattern for creating an apertured topsheet.
Figure 35:
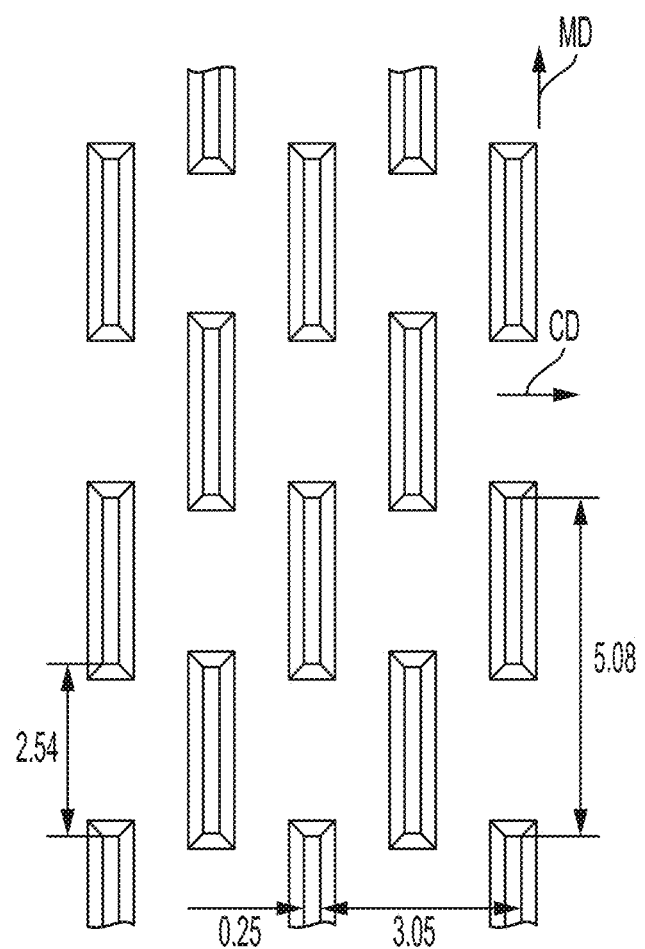
FIG. 35 is a detailed view of the overbond pattern of FIG. 34.

An apertured topsheet 646 is used. The apertured topsheet is a single nonwoven layer of polyethylene/polypropylene bicomponent fibers, made by a process of overbonding and ring rolling (followed by stretching about 40% in the cross-machine direction to open the apertures) as illustrated in FIGS. 2-4 of U.S. Pat. No. 5,628,097 to Benson et al. ("Benson"), and creating the apertured structure illustrated in FIG. 9 of Benson. The over bond pattern is illustrated in FIGS. 34 and 35, with FIG. 35 showing spacing of the overbonding nubs relative to each other in millimeters. The bicomponent fibers have a fiber denier in the range of about 2.5 to about 3. The apertured topsheet has a basis weight of about 28 gsm. The apertured topsheet has a % Percent Effective Area of about 30%, according to the Percent Effective Area Test herein.

The apertured topsheet 646 is cut to a 10.16 by 10.16 centimeters (4 by 4 inch) square size. The apertured topsheet 646 will remain the same for all testing, although a new apertured topsheet will be used for each repetition.

The acquisition material 647 and a high basis weight blotter are weighed to the nearest 0.01 grams. The apertured topsheet 646 is then placed on the high caliper and high air permeability acquisition material of the present disclosure 647.

If the acquisition material 647 is cut from an absorbent article, the acquisition material 647 should include only the acquisition material and not portions of the absorbent core, distribution material (if provided), or the topsheet. Care must be taken when removing the acquisition material 647 from the absorbent article not to destroy the acquisition material 647 or cause unintended gross deformation of the acquisition material. If difficulty is encountered in removing the acquisition material 647 from the absorbent article, the acquisition material 647 and the surrounding portion of the absorbent article may be frozen. Freezing may be accomplished using PH100-15 circuit refrigerant made by Philips ECG, Inc. of Waltham, Mass.

The acquisition material 647 is, in turn, placed upon a high basis weight blotter after weighing (not shown). The high basis weight blotter is made of wet-laid 100% virgin cellulose fibers having a basis weight of 0.0925 grams per square inch and a caliper of about 0.75 millimeters (0.030 inches). A suitable blotter is number 989 filter paper made by Eaton-Dikeman Division of Knowlton Brothers of Mt. Holly Springs, Pa. The apertured topsheet is then centered on top of the acquisition material (i.e., the acquisition material is sandwiched between the topsheet and the blotter).

The cylinder 640 is centered on the apertured topsheet 446. A syringe having an opening of 5 to 6 millimeters dispenses 20 cubic centimeters (manually) of test fluid through the hole in the cylinder 640 onto the top of the apertured topsheet 646. The test fluid is an analog formulated as described below. The 100.6 gram weight 644 is inserted through the hole in the cylinder 640 and gently placed on the test fluid, rotated clockwise 180 degrees to evenly spread the test fluid on the surface of the topsheet, and allowed to sit for a period of 2 minutes.

After 2 minutes, the weight 644 is removed from the apertured topsheet 646. The apertured topsheet 646 is removed from the acquisition material 647 by dragging the apertured topsheet 646 parallel to the acquisition material 647. Both the acquisition material 647 and the high basis weight blotter are then weighed. The trans-topsheet capacity is the increase in combined weight of the acquisition material 647 and the high basis weight blotter, caused by the test fluid penetrating through the apertured topsheet 646 on a unit area basis, divided by the apertured topsheet 646 test area of 3.142 square inches. Five replicates are done and the results are reported to the nearest 0.1 g/in$^2$.

The test fluid is an analog made by mixing 3 percent by weight Carbopol 941 available from the B. F. Goodrich Corporation of Brecksville, Ohio, or an equivalent acrylic polymer, in distilled water for five minutes using a hand held electric mixer. The mixture is allowed to equilibrate for at least 12 hours and used for the trans-topsheet penetration test within 72 hours.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. An absorbent article comprising:
    a liquid permeable topsheet;
    a liquid impermeable backsheet;
    an absorbent core disposed at least partially intermediate the topsheet and the backsheet; and
    an acquisition material disposed at least partially intermediate the topsheet and the absorbent core;
    wherein the acquisition material has:
        a Caliper in the range of about 3.5 mm to about 10 mm, according to the Caliper Test; and
        an Air Permeability in the range of about 6,100 l/m$^2$/s to about 10,000 l/m$^2$/s, according to the Air Permeability Test;
        wherein the acquisition material comprises two or more layers; and
        wherein a first layer of the acquisition material is not bonded to a second layer of the acquisition material.

2. The absorbent article of claim 1, wherein the acquisition material comprises:
    a first surface;
    a second surface; and
    three-dimensional features extending outwardly from the first surface.

3. The absorbent article of claim 2, wherein the three-dimensional features extend toward the absorbent core.

4. The absorbent article of claim 2, wherein the three-dimensional features extend toward the topsheet.

5. The absorbent article of claim 2, wherein at least a majority of the three-dimensional features have an area in the range of about 30 mm$^2$ to about 100 mm$^2$.

6. The absorbent article of claim 2, wherein at least a majority of the three-dimensional features have a largest dimension in the range of about 2 mm to about 20 mm.

7. The absorbent article of claim 2, wherein the first layer of the acquisition material or the second layer of the acquisition material comprises the three-dimensional features.

8. The absorbent article of claim 7, wherein the first layer and the second layer comprise the three-dimensional features, and wherein tips of the three-dimensional features of the first layer are joined with tips of the three-dimensional features of the second layer.

9. The absorbent article of claim 1, wherein the topsheet defines a plurality of apertures, and wherein a portion of the topsheet is joined to a portion of the acquisition material.

10. The absorbent article of claim 9, wherein the topsheet has a Percent Effective Area in the range of about 5% and about 40%, according to the Percent Effective Area Test.

11. The absorbent article of claim 1, wherein the acquisition material has a Basis Weight in the range of about 40 gsm to about 120 gsm, according to the Basis Weight Test.

12. An absorbent article comprising:
    a liquid permeable topsheet;
    a liquid impermeable backsheet;
    an absorbent core disposed at least partially intermediate the topsheet and the backsheet; and an acquisition material disposed at least partially intermediate the topsheet and the absorbent core;
wherein the acquisition material has:
- a Caliper in the range of about 3.5 mm to about 10 mm, according to the Caliper Test;
- an Air Permeability in the range of about 6,100 $l/m^2/s$ to about 10,000 $l/m^2/s$, according to the Air Permeability Test;
- a first surface;
- a second surface; and
- a plurality of three-dimensional features extending outwardly from the first surface;

wherein the acquisition material comprises two or more layers; and
wherein a first layer of the acquisition material is not bonded to a second layer of the acquisition material.

13. The absorbent article of claim 12, wherein the three-dimensional features extend toward the absorbent core.

14. The absorbent article of claim 12, wherein the topsheet defines a plurality of apertures, and wherein the topsheet is joined to the acquisition material.

15. An absorbent article comprising:
an apertured, liquid permeable topsheet;
a liquid impermeable backsheet;
an absorbent core disposed at least partially intermediate the topsheet and the backsheet; and
an acquisition material disposed at least partially intermediate the topsheet and the absorbent core;
wherein the acquisition material has:
- a Caliper in the range of about 3.5 mm to about 10 mm, according to the Caliper Test;
- an Air Permeability in the range of about 6,100 $l/m^2/s$ to about 10,000 $l/m^2/s$, according to the Air Permeability Test;
- a first surface;
- a second surface; and
- a plurality of three-dimensional features extending outwardly from the first surface; and wherein the acquisition material and the topsheet form a laminate;
wherein the acquisition material comprises two or more layers; and
wherein a first layer of the acquisition material is not bonded to a second layer of the acquisition material.

16. The absorbent article of claim 15, wherein the topsheet has a Percent Effective Area in the range of about 10% to about 30%, according to the Percent Effective Area Test, wherein a majority of the three-dimensional features have areas in the range of about 30 $mm^2$ to about 100 $mm^2$, and wherein the majority of the three-dimensional features have a largest dimension in the range of about 4 mm and about 10 mm.

* * * * *